US012723240B2

(12) United States Patent
Okumura et al.

(10) Patent No.: US 12,723,240 B2
(45) Date of Patent: Sep. 1, 2026

(54) DROPLETS AND METHOD FOR PRODUCING SAME

(71) Applicants: TOHOKU UNIVERSITY, Miyagi (JP); Tokushima University, Tokushima (JP)

(72) Inventors: Masaki Okumura, Miyagi (JP); Motonori Matsusaki, Miyagi (JP); Kenji Inaba, Miyagi (JP); Tomohide Saio, Tokushima (JP); Shingo Kanemura, Hyogo (JP)

(73) Assignees: TOHOKU UNIVERSITY, Miyagi (JP); TOKUSHIMA UNIVERSITY, Tokushima (JP)

( * ) Notice: Subject to any disclaimer, the term of this patent is extended or adjusted under 35 U.S.C. 154(b) by 730 days.

(21) Appl. No.: 17/926,032

(22) PCT Filed: Jun. 4, 2021

(86) PCT No.: PCT/JP2021/021437

§ 371 (c)(1),
(2) Date: Nov. 17, 2022

(87) PCT Pub. No.: WO2021/251306

PCT Pub. Date: Dec. 16, 2021

(65) Prior Publication Data

US 2023/0183671 A1 Jun. 15, 2023

(30) Foreign Application Priority Data

Jun. 9, 2020 (JP) ................................ 2020-100517

(51) Int. Cl.
*C12N 9/90* (2006.01)
*C07K 1/10* (2006.01)

(52) U.S. Cl.
CPC .................. *C12N 9/90* (2013.01); *C07K 1/10* (2013.01); *C12Y 503/04001* (2013.01)

(58) Field of Classification Search
None
See application file for complete search history.

(56) References Cited

U.S. PATENT DOCUMENTS

2001/0034050 A1 10/2001 Chilkoti

OTHER PUBLICATIONS

Wang et al., Human Protein-disulfide Isomerase is a redox-regulated chaperone activated by oxidation of Domaina a, J. Biol. Chem. 287, 2012, 1139-49. (Year: 2012).*

Uniprot, Accession No. P07237, 2020, www.uniprot.org. (Year: 2020).*

Masters, HeLa cells 50 years on, Nature Reviews 2, 2002, 315-19. (Year: 2002).*

Hiller et al., A functional chaperone condensate in the endoplasmic reticulum, Research Square, 2024, doi.org/10.21203/rs.3.rs-4796355/v1. (Year: 2024).*

Uniprot, Accession No. Q15084, 2019, www.uniprot.org. (Year: 2019).*

Galligan et al., The human protein disulfide isomerase gene family, Human Genomics 6, 2012, 6. (Year: 2012).*

Lee et al., Ca2+-driven PDIA6 phase separation to ensure proinsulin quality control, bioRxiv, 2024, doi.org/10.1101/2024.07.30.605722. (Year: 2024).*

Shiraki et al., Effect of additives on liquid droplets and aggregates of proteins, Biophysical Rev. 12, 2020, 587-92. (Year: 2020).*

International Search Report issued Aug. 24, 2021 in International (PCT) Application No. PCT/JP2021/021437.

Langdon, Erin M. et al., "mRNA structure determines specificity of a polyQ-driven phase separation", Science, 2018, vol. 360(6391), pp. 922-927.

Brangwynne, Clifford P. et al., "Active liquid-like behavior of nucleoli determines their size and shape in Xenopus laevis oocytes", Proc. Natl. Acad. Sci. USA, 2011, vol. 108(11), pp. 4334-4339.

Banani, Salman F. et al., "Biomolecular condensates: Organizers of cellular biochemistry", Nat Rev Mol Cell Biol., 2017, vol. 18(5), pp. 285-298.

Kato, Masato et al., "Cell-free Formation of RNA Granules: Low Complexity Sequence Domains Form Dynamic Fibers within Hydrogels", Cell, 2012, vol. 149, pp. 753-767.

Han, Tina W. et al., "Cell-free Formation of RNA Granules: Bound RNAs Identify Features and Components of Cellular Assemblies", Cell, 2012, vol. 149, pp. 768-779.

Iwashita, Kazuki et al., "Coacervates and coaggregates: Liquid-liquid and liquid-solid phase transitions by native and unfolded protein complexes", International Journal of Biological Macromolecules, 2018, vol. 120, pp. 10-18.

Okumura, Masaki et al., "Inhibition of the Functional Interplay between Endoplasmic Reticulum (ER) Oxidoreduclin-1α (Ero1α) and Protein-disulfide Isomerase (PDI) by the Endocrine Disruptor Bisphenol A", Journal Biological Chemistry, 2014, vol. 289, No. 39, pp. 27004-27018.

Okumura, Masaki et al., "A unique leucine-valine adhesive motif supports structure and function of protein disulfide isomerase P5 via dimerization", Structure, 2021, vol. 29, pp. 1357-1370.

Wang, Kan et al., "Phase Separation and Cytotoxicity of Tau are Modulated by Protein Disulfide Isomerase and S-nitrosylation of this Molecular Chaperone", Journal of Molecular Biology, 2020, vol. 432, pp. 2141-2163.

Honjo, Yasuyuki et al., "Protein Disulfide Isomerase P5-Immunopositive Inclusions in Patients with Alzheimer's Disease", Journal of Alzheimer's Disease, 2014, vol. 38, pp. 601-609.

Okumura, Masaki "Discovery, Function and Control Mechanism of Intraventicular Chaperone Separating Liquid Phase", Lecture abstracts of Annual Meeting of the Japanese Biochemical Society, 2020, vol. 93, IS09e-02.

(Continued)

*Primary Examiner* — Todd M Epstein
(74) *Attorney, Agent, or Firm* — Wenderoth, Lind & Ponack, L.L.P.

(57) ABSTRACT

An object to be achieved by the present invention is to prepare a droplet using a protein that has not been known heretofore to form a droplet. The present invention provides a droplet including an assembly of a protein, wherein the protein is a PDI family protein and/or an artificial protein, and contains a thioredoxin-like domain.

6 Claims, 19 Drawing Sheets

Specification includes a Sequence Listing.

(56) References Cited

OTHER PUBLICATIONS

Hamada, Satoshi et al., "Proteomic Analysis of Lipid Droplets in Sesamum indicum", The Protein Journal, 2020, vol. 39, pp. 366-376.
Banani, Salman F. et al., "Biomolecular condensates: Organizers of cellular biochemistry", Nat Rev Mol Cell Biol, 2017, vol. 18, No. 5, pp. 285-298.
Horibe, Tomohisa et al., "Discovery of Protein Disulfide Isomerase P5 Inhibitors that Reduce the Secretion of Mica from Cancer Cells", Chem Bio Chem, 2014, vol. 15, pp. 1599-1606.
Shiraki, "An effect of additives on protein aggregation and liquid-liquid phase separation", Seibutsu kogakkaishi, 2020, vol. 98, No. 5, pp. 251-254.
Extended European Search Report issued Oct. 17, 2023 in corresponding European Patent Application No. 21822923.5.
Okumura et al., "Dynamic assembly of protein disulfide isomerase in catalysis of oxidative folding", Nature Chemical Biology, 2019, vol. 15, No. 5, pp. 499-509.

* cited by examiner

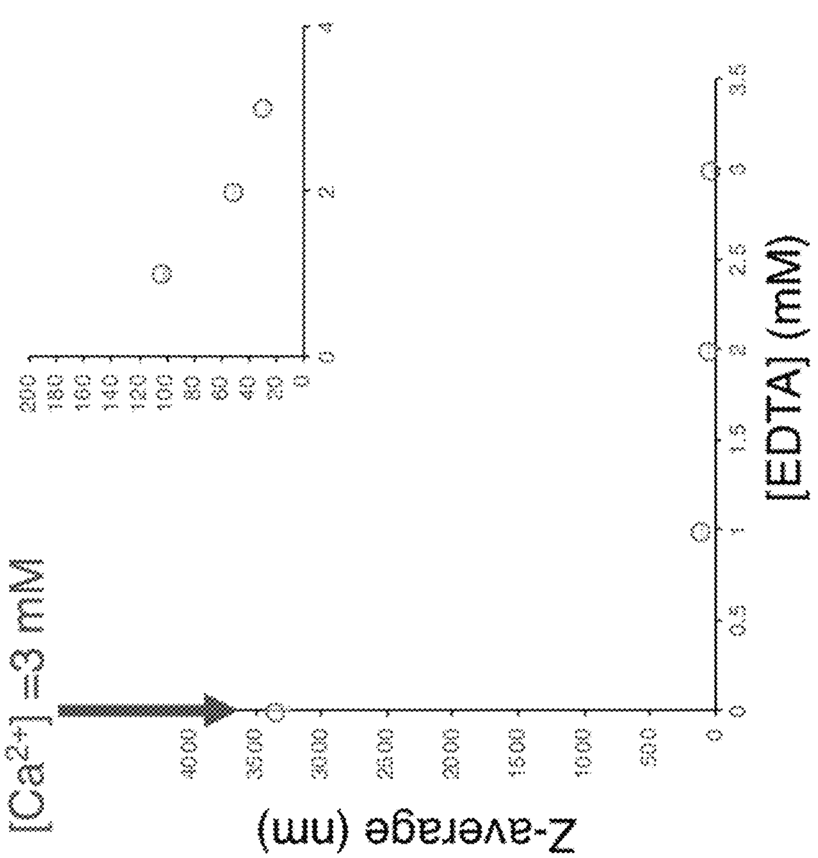
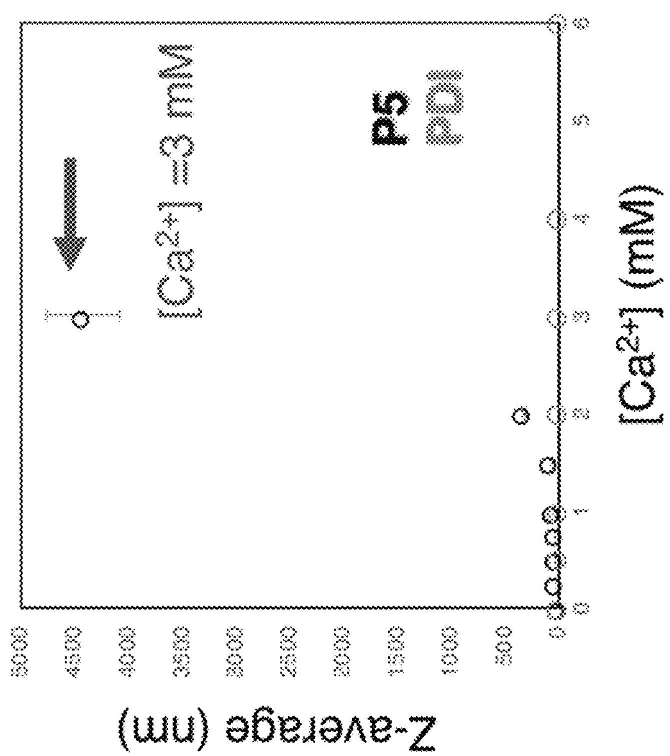
Fig. 2

Fig. 3
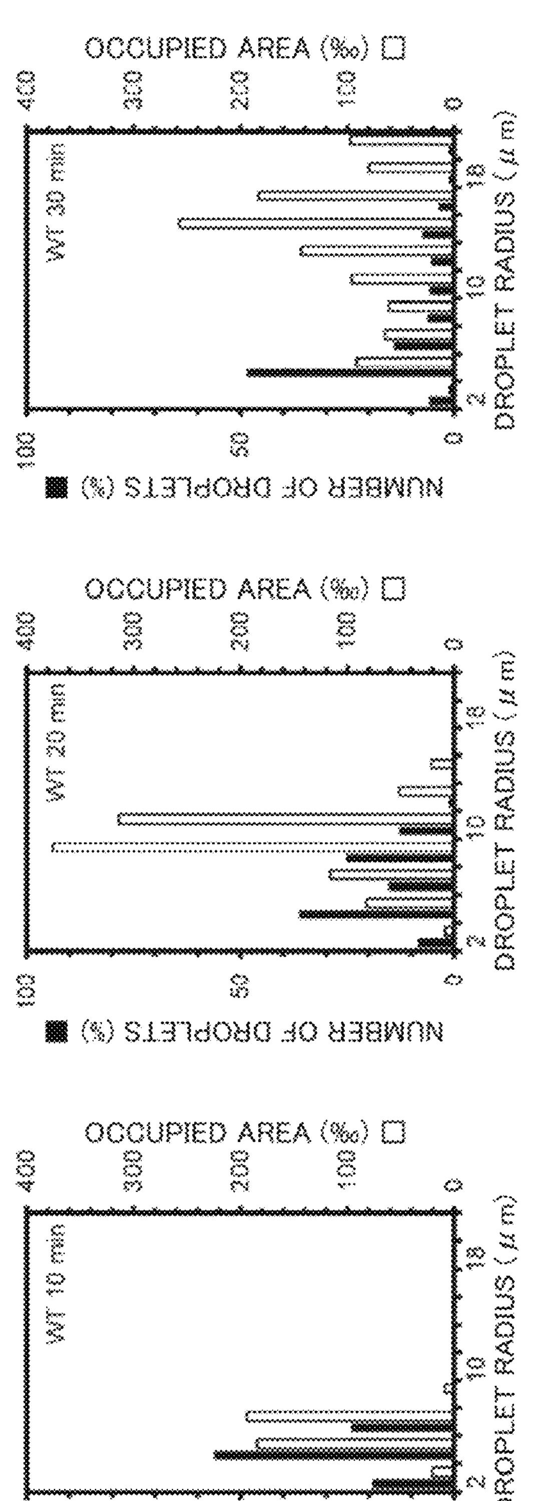
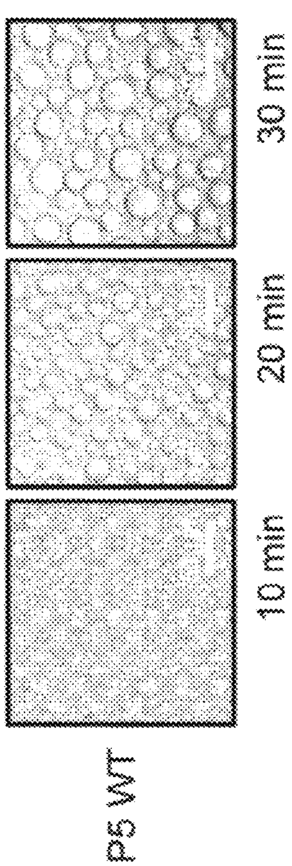

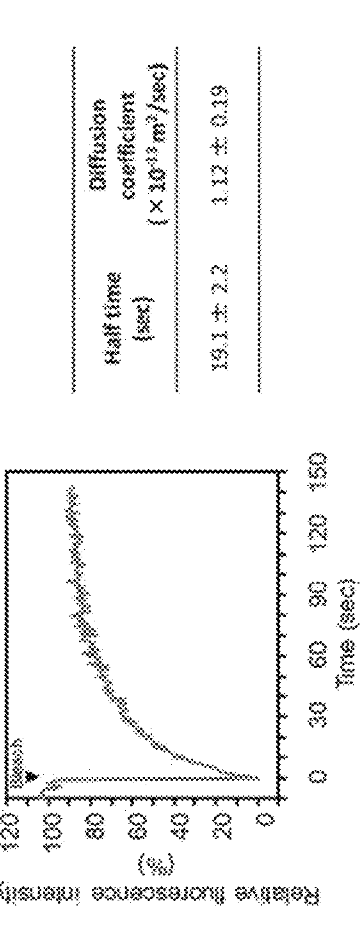
| Half time (sec) | Diffusion coefficient ($\times 10^{-13}$ m$^2$/sec) |
| --- | --- |
| 19.1 ± 2.2 | 1.12 ± 0.19 |
Fig. 4

Fig.14
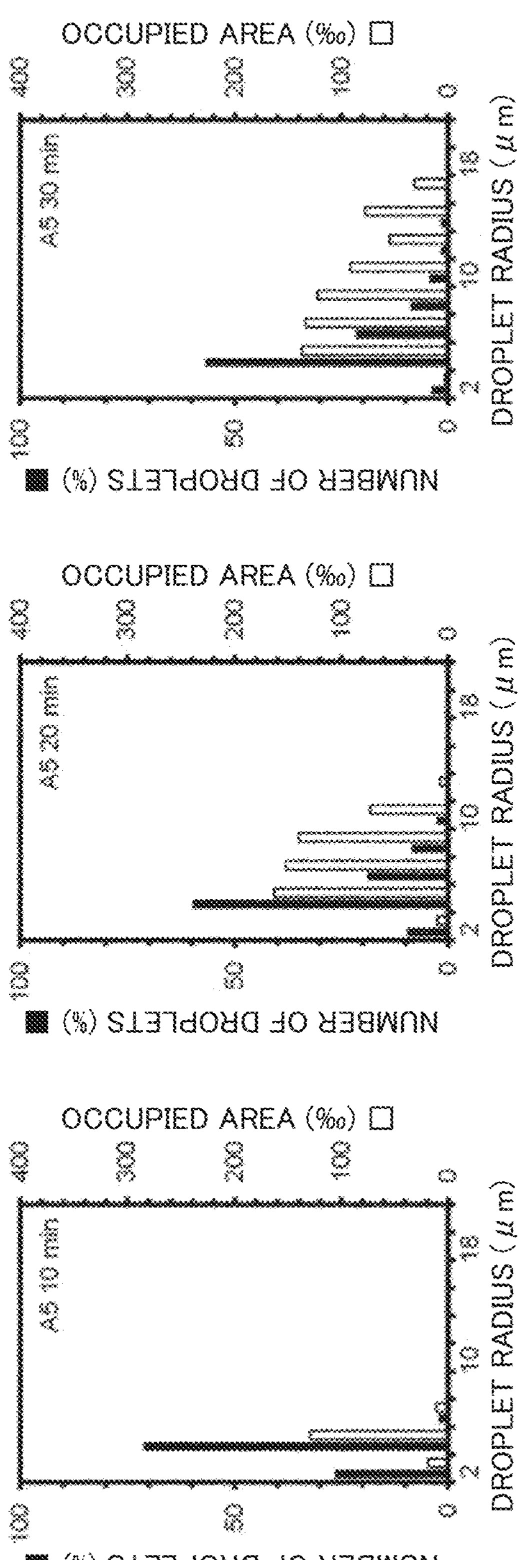
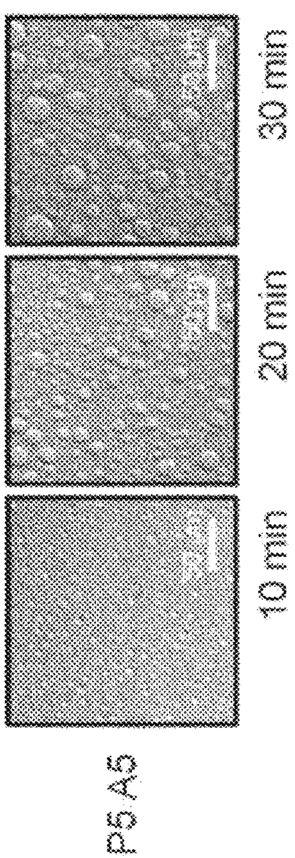

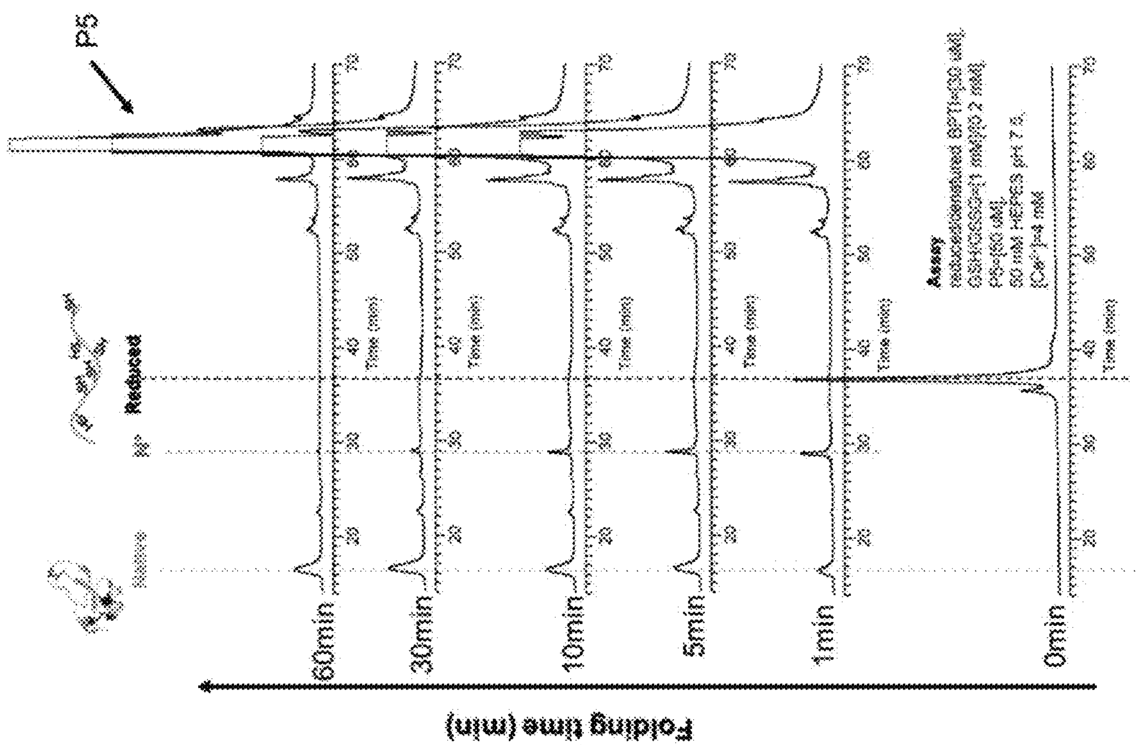
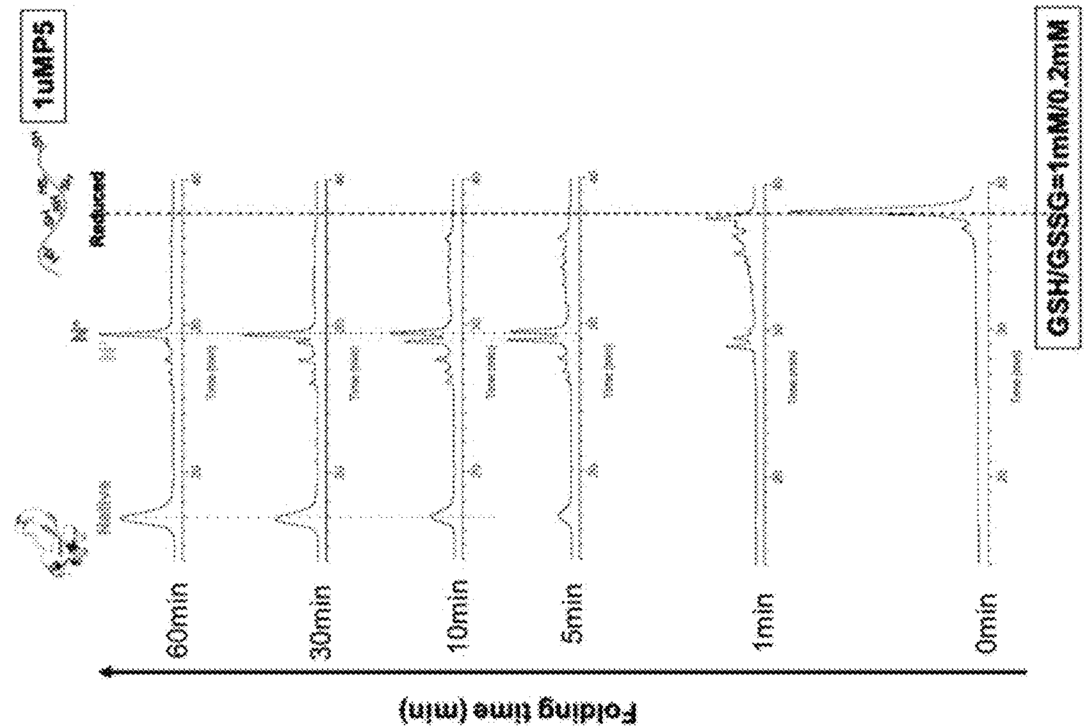
Fig.16

Fig.20

```
                          |→   signal sequence  ←||→   a0 domain
SEQ ID NO: 8  HUMAN ------------MALLVLGLVSCTF-FLAVNGLYSSSDDVIELTPSNFNREVIQSDSLWLVEFYAPWCGHCQRLTPEWKKAATALKDVV 76
SEQ ID NO: 9  MOUSE ------------MARLVLGLVSCTF-YLAVSGLYSSSDDVIELTPSNFNREVIQSDGLWLVEFYAPWCGHCQRLTPEWKKAATALKDVV 76
SEQ ID NO:10  CHICK -------MGVAGTGGLWWGTVSCTL-FLAVNGLYSASDDVIELTPTNFNKEVIQSESLWLVEFYAPWCGHCQRLTPEWKKAATALKGVV 81
SEQ ID NO:11  BOVIN RRRLRCVAARALGMARLVLGLMSCTL-FITVNGLYSSSDDVIELTPSNFNREVIQSDSLWLVEFYAPWCGHCQRLTPEWKKAATALKDVV 89
SEQ ID NO:12  RABIT ------------MALLGLGLVSCTF-FLAVNGLYSSSDDVIELTPSNFNREVIQSDSLWLVEFYAPWCGHCQRLTPEWKKAASALKDVV 76
SEQ ID NO:13  ICTPU -------------MRAFFGVLACSLTVLSVNGLYSASDDVIELNPSNFNREVLQSDSLWLVEFYAPWCGHCQSLVPEWKKAATALKGVV 76
SEQ ID NO:14  DANRE -------------MRALLGVLACSLTVLSAYGLYTSSDDVVELNPSNFNREVIQSDSLWLVEFYAPWCGHCKSLAPEWKKAATALKGIV 76

                             a0 domain    ←|                                    |→   a domain
KVGAVDADKHHSLGGQYGVQGFPTIKIFGSNKNRPEDYQGGRTGEAIVDAALSALRQLVKDRLGGRSGGYSSGKQGRSD-SSSKKDVIELTDDSFD 171
KVGAVNADKHQSLGGQYGVQGFPTIKIFGANKNKPEDYQGGRTGEAIVDAALSALRQLVKDRLGGRSGGYSSGKQGRGD-SSSKKDVVELTDDTFD 171
KVGAVDADKHQSLGGQYGVRGFPTIKIFGANKNKAEDYQGGRTSEAIVDAALSALRSLVKDRLSGRSGGYSSGRQSRESGGGDKKDVIELTDDSFD 177
KVGAVDADKHQSLGGQYGVQGFPTIKIFGSNKNKPEDYQGGRTGEAIVDAALSALRQLVKDRLGGRGSGYSSGKQGRGD-SSSKKDVIELTDDNFD 184
KVGAVDADKHQALGGQYGVQGFPTIKIFGANKNRPEDYQGGRTGEAIVDAALSALRQLVKDRLGGRSGSHSSGRQGRGD-SASKKDVIELTDDSFD 171
KVGAVDADQHKSLGGQYGVRGFPTIKIFGANKHKPEDYQGGRSSQAIVEAALNAARSLVKDRLSGKSGGSDYSRQSS-GG-GNKKDVVELTDDNFD 170
KVGAVDADQHNSLGGQYGVRGFPTIKIFGGNKHKPEDYQGGRTNQAIVDAALNALRSLVKDRLGGKTGGSDYSRQSG-GGAGNKKDVVELTDDNFD 165

                                                                              a domain    ←|
KNVLDSEDVWMVEFYAPWCGHCKNLEPEWAAAASEVKEQTKGKVKLAAVDATVNQVLASRYGIRGFPTIKIFQKGESPVDYDGGRTRSDIVSRALD 267
KNVLDSEDVWMVEFYAPWCGHCKNLEPEWAAAATEVKEQTKGKVKLAAVDATVNQVLASRYGIKGFPTIKIFQKGESPVDYDGGRTRSDIVSRALD 267
KNVINSDDVWMVEFYAPWCGHCKNLEPEWAAAATEVKEQTKGKVKLAAVDATVNQMLANRYGIRGFPTIKIFQKGEDPVDYDGGRTRSDITARALD 273
KNVLDSEDVWMVEFYAPWCGHCKNLEPEWAAAATEVKEQTKGKVKLAAVDATVNQVLASRYGIRGFPTIKIFQKGESPVDYDGGRTRSDIVSRALD 280
ENVLESDDIWMVEFYAPWCGHCKNLEPEWAAAATEVKEQTKGKVKLAAVDATVNQMLSSRYGIRGFPTIKIFQKGESPVDYDGGRTRSDIVSRALD 267
RMVLDGDAVWMVEFFAPWCGHCKNLEPEWTAAATQVKEQTSGRVKLGAVDATVHQGLASRYGIKGFPTIKIFRKGEEPEDYQGGRTRSDIIARAID 266
RTVLESDDVWLVEFFAPWCGHCKNLEPEWTAAATEVKEQTKGKVKLAAVDATVHQGLASRFGIRGFPTIKVFRKGEEPEDYQGGRTRSDIVARALE 267

   |→   b domain
LFSDNAPPPELLEIINEDIAKRTCEEHQLCVVAVLPHILDTGAAGRNSYLEVLLKLADKYKKKMWGWLWTEAGAQSELETALGIGGFGYPAMAAIN 363
LFSDNAPPPELLEIINEDIAKKTCEEHQLCVVAVLPHILDTGAAGRNSYLEVLLKLADKYKKKMWGWLWTEAGAQYELENALGIGGFGYPAMAAIN 363
LFSDNAPPPELLEIINEDVLKTTCDAHQLCIISVLPHILDTGASGRNSYLDVMLKMAEKYKKKMWGWLWTEAGAQSDLESSLGIGGFGYPAMAAIN 369
LFSDNAPPPELLEIINEDVAKKTCEEHQLCVVAVLPHILDTGAAGRNSYLEVLLKLADKYKKKMWGWLWTEAGAQSELENALGIGGFGYPAMAAIN 376
LFSDNAPPPELLEIVNEDVAKRACEEHQLCIVAVLPHILDTGAAGRNSYLDVLLKLADKYKKKMWGWLWTEAGAQAELESALGIGGFGYPAMAAIN 363
LFSDNAPPPELLEILNEDILKKTCEDHQLCIIAVLPHILDTGAAGRNAYLEVMMKMAEKYKKKMWGWLWTESGAQMELEASLGIGGFGYPAMAAIN 362
LYSDNIPAPELQEVLNEGILKKTCEDYQLCIIAVLPHILDTGASGRNSYLEVMKTMAEKYKKKMWGWLWTEAGAQMELEASLGIGGFGYPAMAAIN 363

  b domain   ←|                              |→      E/D rich region        ←|
ARKMKFALLKGSFSEQGINEFLRELSFGRGSTAPVGGGAFPTIVEREPWDGRDGELPVEDDIDLSDVELDDLG-KDEL 440
ARKMKFALLKGSFSEQGINEFLRELSFGRGSTAPVGGGSFPTITPREPWDGKDGELPVEDDIDLSDVELDDLE-KDEL 440
ARKMKFALLKGSFSEQGINEFLRELSVGRGSTAPVGGGAFPKIHAVEPWDGKDGELPVEDDIDLSDVDLDDIWDKDEL 447
ARKMKFALLKGSFSEQGINEFLRELSFGRGSTAPVGGGAFPTISTREPWDGKDGELPVEDDIDLSDVELDDLE-KDEL 453
ARKMKFALLKGSFSEQGINEFLRELSFGRGSTAPVGGGVFPAISVRDPWDGQDGVLPVEDDIDLSDVELDDLE-KEEL 440
ARKMKFALLKGSFSETGIYEFLRDLSVGRGSTATITGGALPKIHTVEAWDGKDGVLPVEDDIDLSDVDLDDLD-KDEL 439
SRKMKFALLKGSFSETGIHEFLRELSVGRGSTATVGGGALPKINTVQAWEGKDGELPMEDDIDLSDVDLDDLE-KDKL 440
```

DROPLETS AND METHOD FOR PRODUCING SAME

INCORPORATION BY REFERENCE OF SEQUENCE LISTING

A sequence listing in electronic (ASCII text file) format is filed with this application and incorporated herein by reference. The name of the ASCII text file is "ATTCHG_Sequence_Listing-2215.txt"; the file was created on Nov. 17, 2022; the size of the file is 33,733 bytes.

TECHNICAL FIELD

Cross-Reference to Related Application

This application claims priority from Japanese Patent Application No. 2020-100517, filed on Jun. 9, 2020, the entire disclosure of which is incorporated herein by reference. The present invention relates to a droplet and a method of producing the same.

BACKGROUND ART

A droplet is beginning to be known as a multi-stage reaction field for a sequential enzymatic reaction or the like, and in terms of its constituent factors, is known to be formed through addition of a second messenger by RNA, DNA, ATP, or the like to a natively unstructured protein called an intrinsically disordered protein. FUS, which is a typical example capable of forming a droplet, is known to be such that a low complexity domain (LC domain) thereof, in which a structureless sequence appears repeatedly, forms a core of the droplet. A chaperone is known as a factor for controlling formation/dissociation of the droplet, and is also reported to be contained in the droplet. The term "chaperone" collectively refers to a group of proteins that control aggregation of proteins. However, there is no example in which a protein having functions as a chaperone and an enzyme forms a droplet by itself. A thioredoxin is known as a domain of a protein having imparted thereto two or more functions of a chaperone and an enzyme. The "thioredoxin" is a low-molecular-weight redox protein, and is known to play an important role in various life reactions by promoting reduction/cleavage of a disulfide bond formed by a cysteine residue of another protein.

CITATION LIST

Non-Patent Literature

NPL 1: Science, 360 (6391), 922-927 (2018)
NPL 2: Proc. Natl. Acad. Sci. USA, 108 (11), 4334-4339 (2011)
NPL 3: Nat. Rev. Mol. Cell Biol., 18 (5), 285-298 (2017)
NPL 4: Cell, 149 (4), 753-767 (2012)
NPL 5: Cell, 149 (4), 768-779 (2012)
NPL 6: Int. J. Biol. Macromol., 10 (PtA), 10-18 (2018)
NPL 7: J. Biol. Chem.; 289 (39): 27004-18 (2014)
NPL 8: Structure, 29, 1-14 (2021)

SUMMARY OF INVENTION

Technical Problem

As it has not been known heretofore that a protein having chaperone and enzyme functions forms a droplet by itself, an object of the present invention is to develop a technology for preparing such droplet.

Solution to Problem

Under such circumstances, the inventors of the present invention have made extensive investigations, and as a result, have found that a droplet can be produced by using a protein containing one or more thioredoxin-like domains. On the basis of such novel finding, the inventors of the present invention have investigated factors for forming a droplet, a preferred structure of the protein containing a thioredoxin-like domain, and other conditions. Thus, the inventors have completed the present invention.

Thus, the present invention provides the following items:

Item 1. A droplet including an assembly of a protein, wherein the protein is a PDI family protein and/or an artificial protein, and contains a thioredoxin-like domain.

Item 2. The droplet according to Item 1, wherein the protein has a calcium-binding region.

Item 3. The droplet according to Item 1 or 2, wherein the protein has two or more thioredoxin-like domains, wherein at least two of the two or more thioredoxin-like domains are bound to each other via a linker, and wherein the linker contains at least one kind of amino acid residue selected from the group consisting of: serine; glycine; proline; glutamic acid; glutamine; aspartic acid; asparagine; arginine; lysine; and tyrosine.

Item 4. The droplet according to any one of Items 1 to 3, wherein the protein is a dimer or a higher multimer.

Item 5. The droplet according to any one of Items 2 to 4, wherein the PDI family protein is P5.

Item 6. A method of producing a droplet including a step of assembling a protein in the presence of a calcium ion, the protein being a PDI family protein and/or an artificial protein, and containing a thioredoxin-like domain, the protein further having a calcium-binding region.

Item 7. The method according to Item 6, wherein at least two of the two or more thioredoxin-like domains are bound to each other via a linker, and wherein the linker contains at least one kind of amino acid residue selected from the group consisting of: serine; glycine; proline; glutamic acid; glutamine; aspartic acid; asparagine; arginine; lysine; and tyrosine.

Item 8. The method according to Item 6 or 7, wherein the PDI family protein is a dimer or a higher multimer.

Item 9. The method according to any one of Items 6 to 8, wherein the PDI family protein is P5.

Advantageous Effects of Invention

According to the present invention, the droplet can be prepared using a protein that has not been known heretofore to form a droplet. As described later, typically, in a droplet, its constituent proteins interact at such a distance as to be able to be brought into contact with each other while having fluidity, and hence, for example, when a substance serving as a reaction raw material is added, the substance can enter between the constituent proteins of the droplet to be concentrated in the vicinity of the thioredoxins of the constituent proteins. Accordingly, the droplet of the present invention is useful for, for example, use as a reaction field for the enzymatic reaction or disaggregation reaction of thioredoxins or the like, or the storage of a defective protein. Hitherto, there has been no example in which a protein having thioredoxin activity forms a droplet by itself, and hence the present invention is extremely useful for an enzymatic reaction or a disaggregation reaction.

BRIEF DESCRIPTION OF DRAWINGS

The upper left part of FIG. 1 shows SDS-PAGE results of a purified protein, and shows that the protein is a high-purity purified product. The right part is an illustration of the configuration of thioredoxin-like domains of a PDI family used and SS exchange active sites thereof. The lower left part shows a change in particle diameter by DLS. Among the PDI family, P5 associates in a calcium-dependent manner.

The left part of FIG. 2 is a graph obtained by scaling up the long axis of the particle diameter of FIG. 1 to 5,000 nm. P5 forms associated bodies of about 4,500 nm in the presence of 3 mM calcium. The right part of FIG. 2 shows the results of titration of the associated bodies produced in the left part with EDTA. The P5 associated bodies return to non-associated bodies along with the titration, meaning the presence of reversibility.

FIG. 3 shows with a phase-contrast microscope that the associated bodies of P5 are spherical. Along with a time change, the spherical associated bodies fuse together, and the spherical associated bodies grow larger.

The images of FIG. 4 show the results of overlaying of fluorescence microscope images and phase-contrast microscope images. When an intense laser is applied, spherical assemblies that have undergone fluorescence bleaching once undergo fluorescence recovery along with a time change. The lower part of FIG. 4 shows the results of analysis of fluorescence recovery, indicating that a half time is about 19 seconds. This FRAP experiment supports that the spherical associated bodies are droplets.

Figure 5:
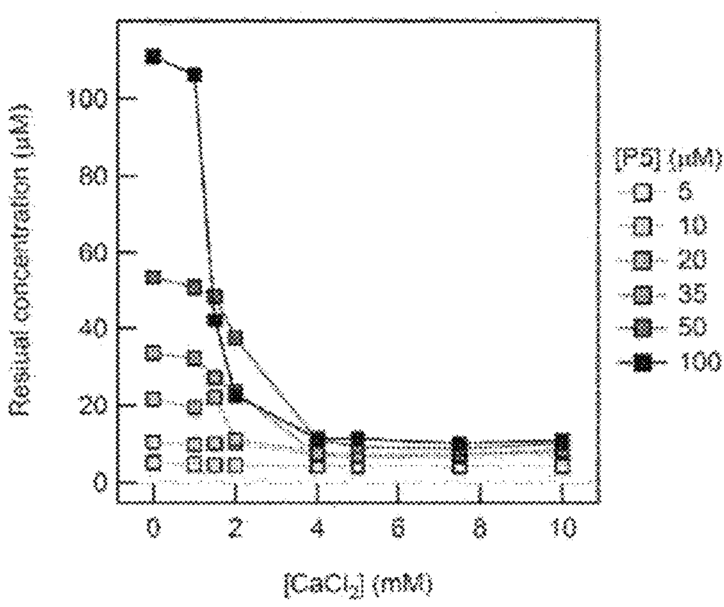

FIG. 5 shows the concentrations of supernatant fractions obtained by mixing calcium and P5 at various concentrations and then centrifuging the mixtures.

Figure 6:
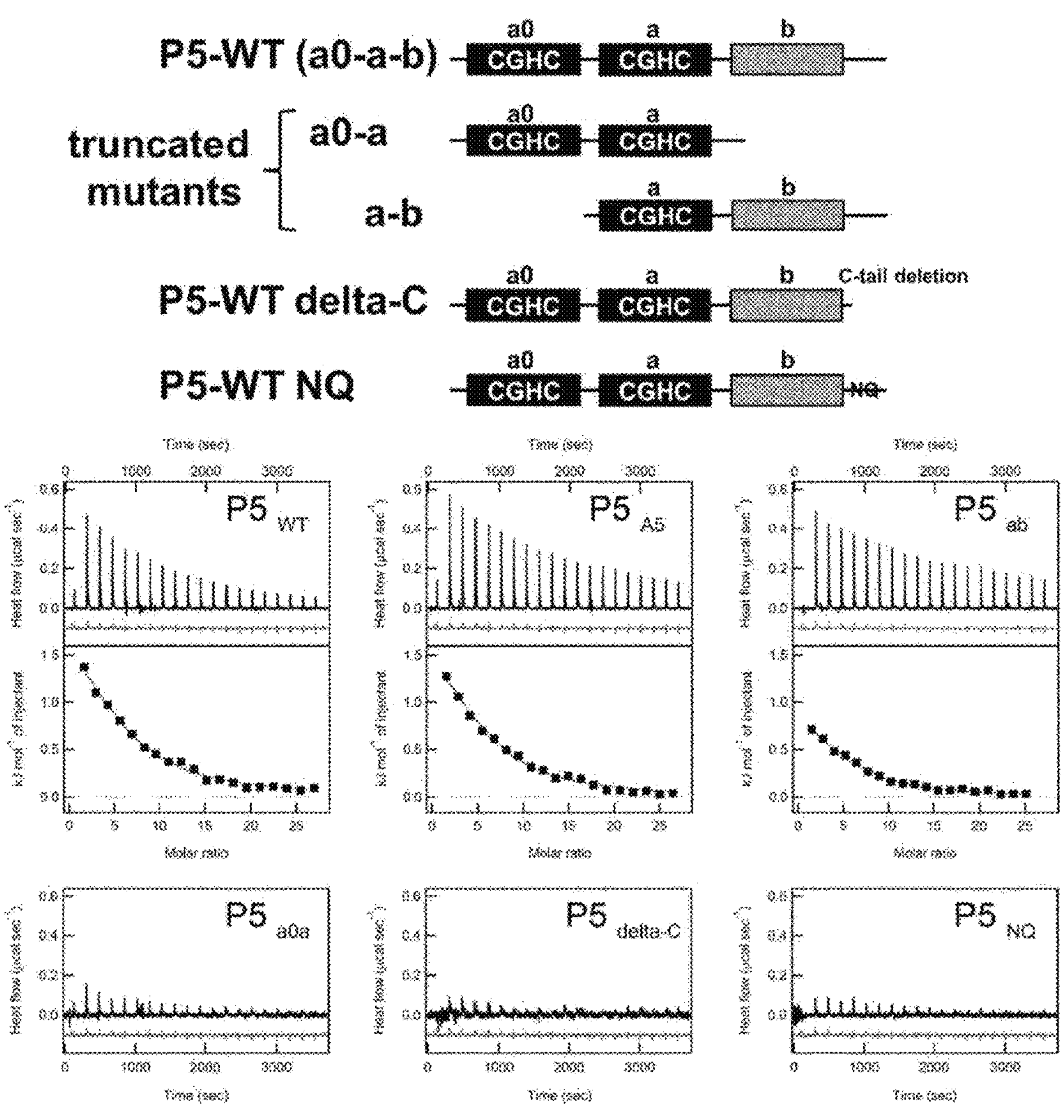

FIG. 6 shows the determination of the calcium-binding region of P5 by ITC measurement. Various mutants of P5 are illustrated in the upper part of FIG. 6, and the results of an ITC experiment of each mutant and calcium are shown in the lower part of FIG. 6. An upward heat quantity represents a heat quantity due to binding, and an unstructured region positioned at the C-terminus was found to be the calcium-binding region.

Figure 7:
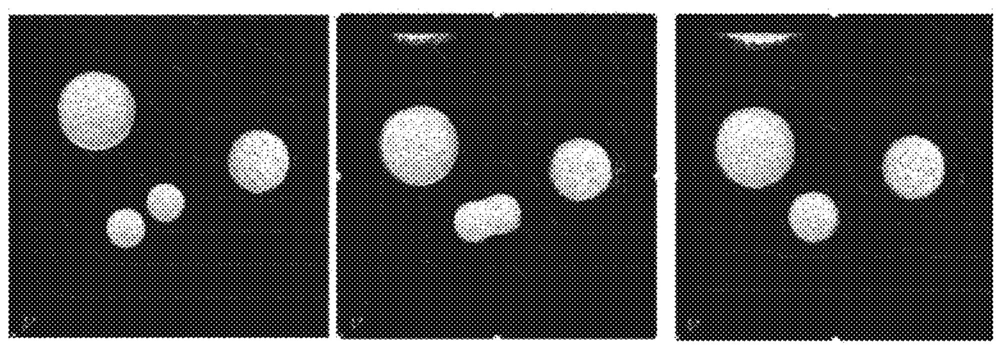

FIG. 7 shows real-time observation of droplets using a fluorescence microscope capable of measuring a refractive index. An image capturing the moment droplets are about to fuse together is shown at the center. In addition, droplet surfaces are relatively rough, meaning high fluidity.

Figure 8:
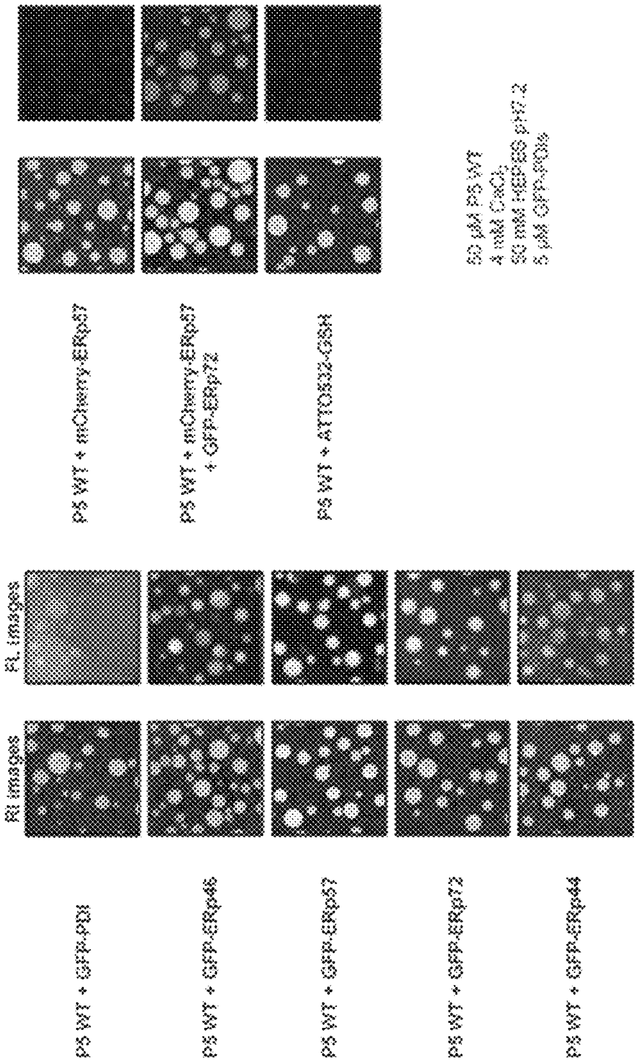

FIG. 8 shows that various enzymes/chaperones and glutathione can be concentrated inside droplets. FIG. 8 supports the state of being droplets with a refractive index (RI), and indicates localization with various enzymes/chaperones and glutathione that are fluorescently labeled. It is shown that ERp46, ERp72, ERp57, and ERp44, which are enzymes/chaperones localized in the endoplasmic reticulum, are easily concentrated inside the droplets, but PDI hardly enters the inside of the droplets. In addition, it is shown that, through use of mCherry-ERp57 and GFP-ERp72, at least two kinds of enzymes/chaperones can be concentrated inside the droplets. In addition, glutathione labeled with ATTO 532 can also be concentrated inside the droplets.

Figure 9:
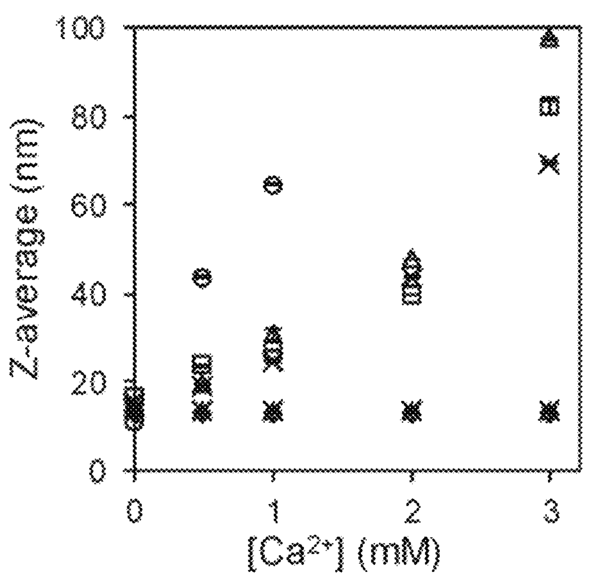

FIG. 9 shows pH dependence in droplet formation. A pH of 7.4 or less is preferred for droplet formation.

Figure 10:
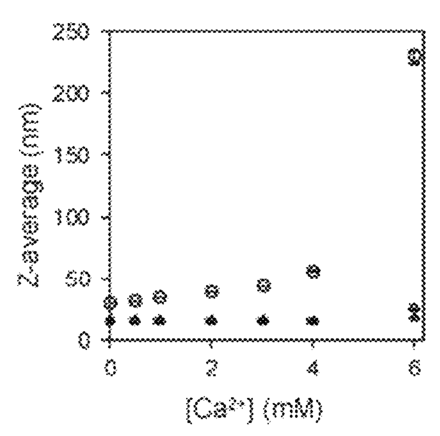

FIG. 10 shows temperature dependence in droplet formation. A lower temperature is preferred for droplet formation.

Figure 11:
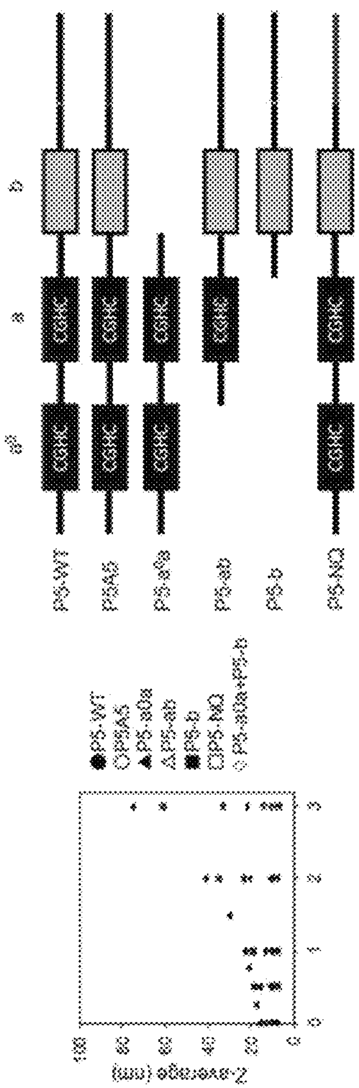

FIG. 11 shows the importance of domains of P5 in droplet formation. Full-length P5 is preferred for droplet formation.

Figure 12:
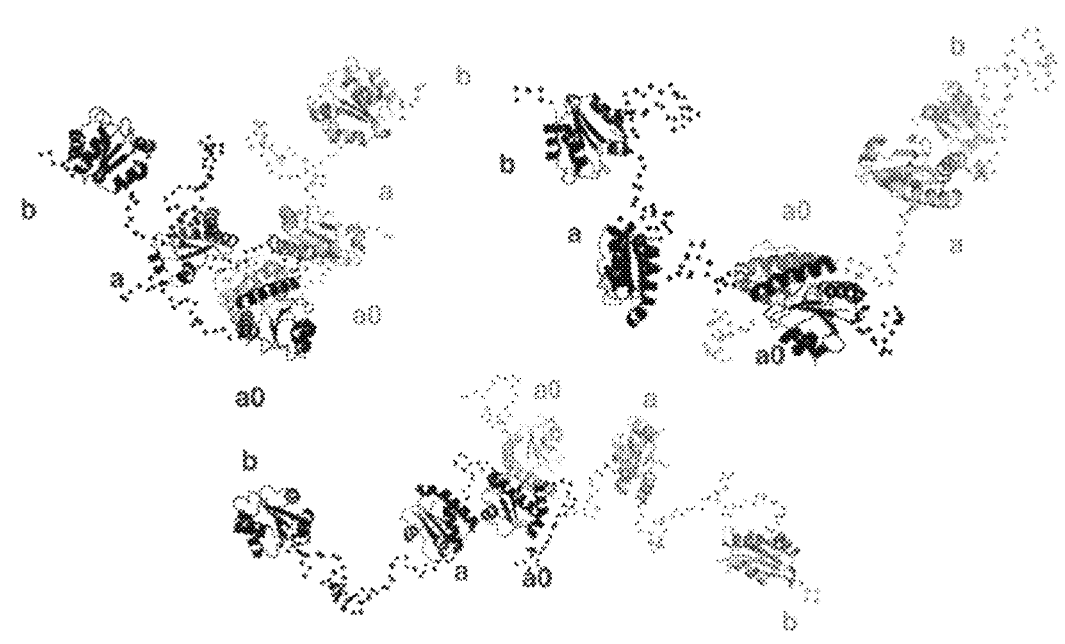

FIG. 12 shows a novel structure of P5. Flexibility between thioredoxin-like domains is relatively high. In addition, a dimer is formed in a solution.

Figure 13:
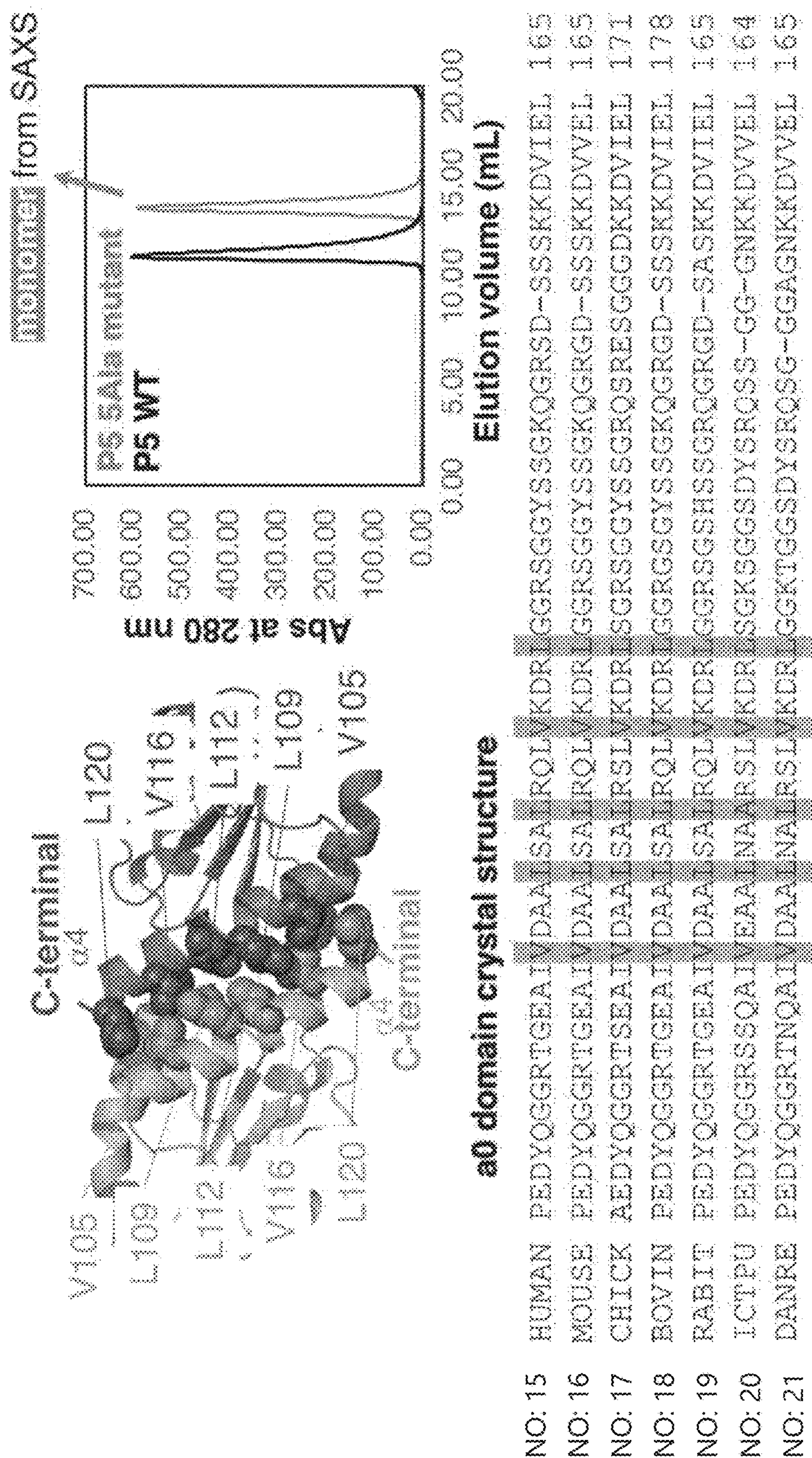

The upper part of FIG. 13 reveals from a crystal structure that dimer formation of P5 uses as a driving force a leucine zipper motif positioned in the 4th α-helix in an a0 domain at the beginning. Accordingly, the substitution of this site with alanine gives a monomer in a solution (lower part of FIG. 13).

FIG. 14 shows with a phase-contrast microscope that associated bodies of a P5 monomer can form droplets as with a wild type.

Figure 15:
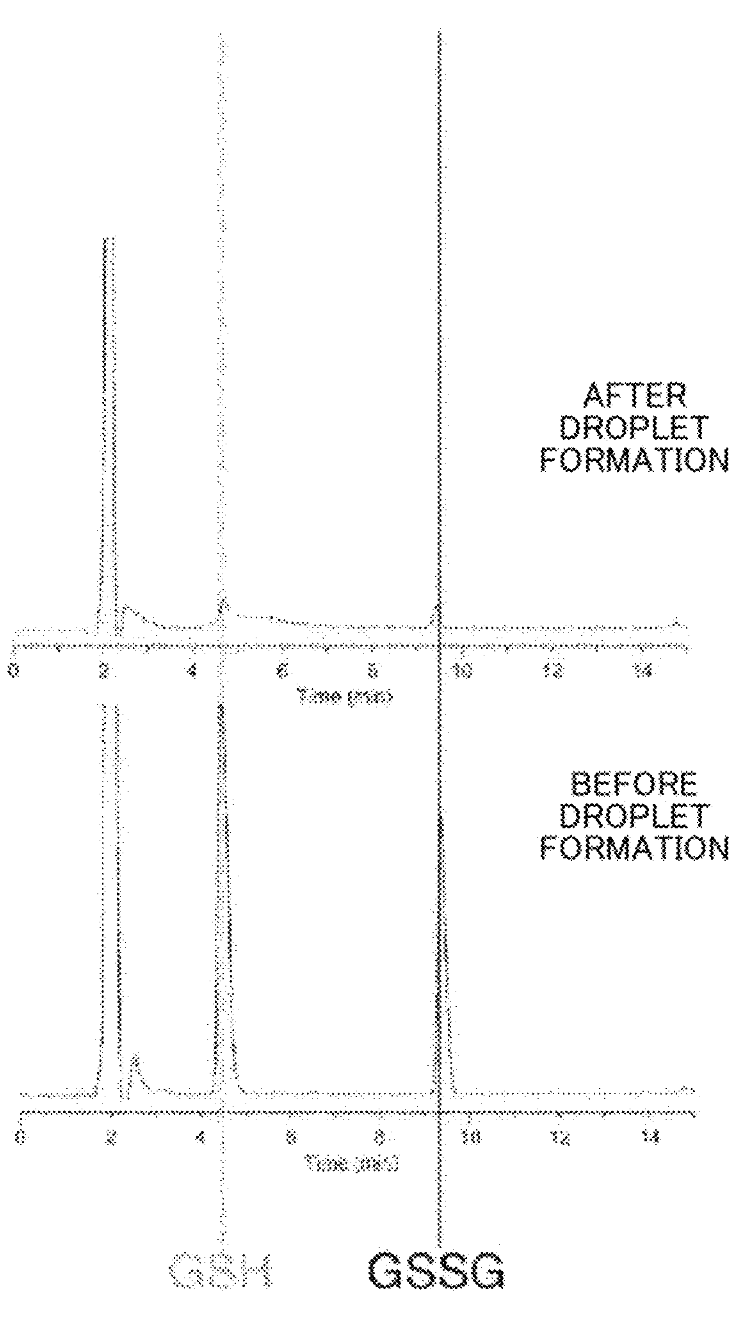

FIG. 15 shows the concentration of glutathione by P5 droplets. Reversed-phase HPLC was used for the separation of glutathione. It is found that, after droplet formation, nearly all glutathione disappeared.

FIG. 16 shows substrate oxidative folding catalysis by P5 droplets. Reversed-phase HPLC was used for the folding state of a substrate. It is found that, after droplet formation, nearly all of a reduced and denatured substrate disappeared immediately after an oxidative folding reaction.

Figure 17:
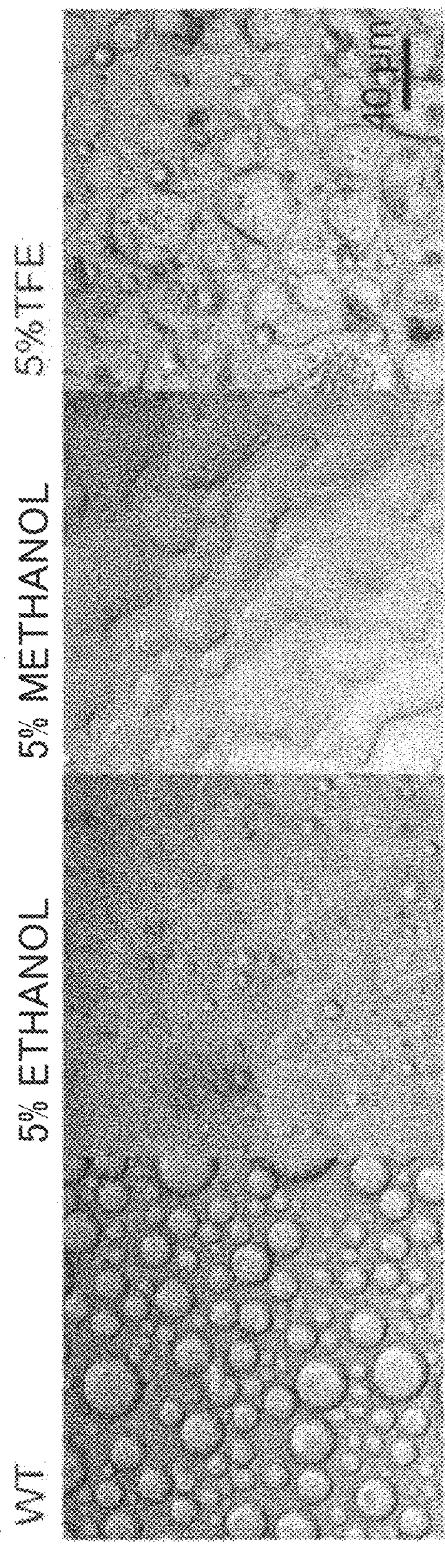

FIG. 17 shows examples of application of organic solvents to P5 droplets. Various organic solvents were added in v/v, and observation was performed with a phase-contrast microscope.

Figure 18:
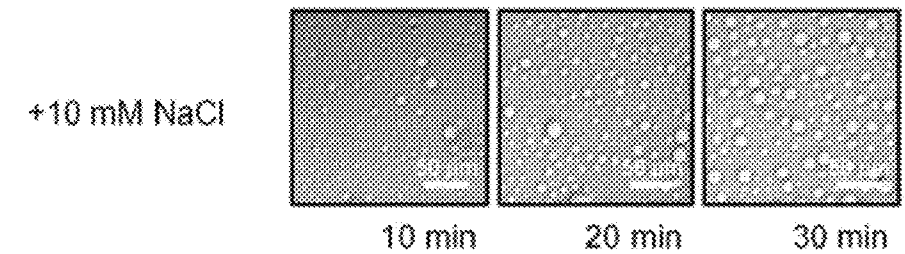

FIG. 18 shows the effect of salt on P5 droplets. Observation was performed with a phase-contrast microscope. Salt influences the size of droplet formation as compared to the salt-free conditions of FIG. 3, and hence is a control factor for the size of droplet formation.

Figure 19:
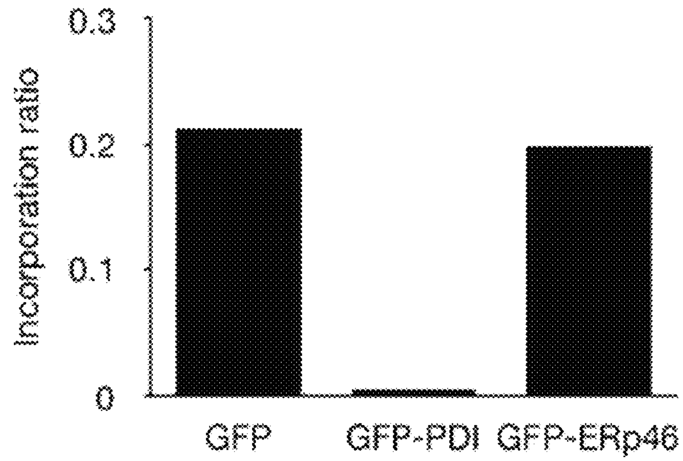

FIG. 19 shows the degree of incorporation into the inside of droplets. Various PDI family members fluorescently labeled with GFP were produced, and the degrees of their incorporation were evaluated. The results reveal that PDI is hardly incorporated and ERp46 is easily incorporated.

FIG. 20 shows the amino acid sequences of P5 of various organisms.

Figure 21:
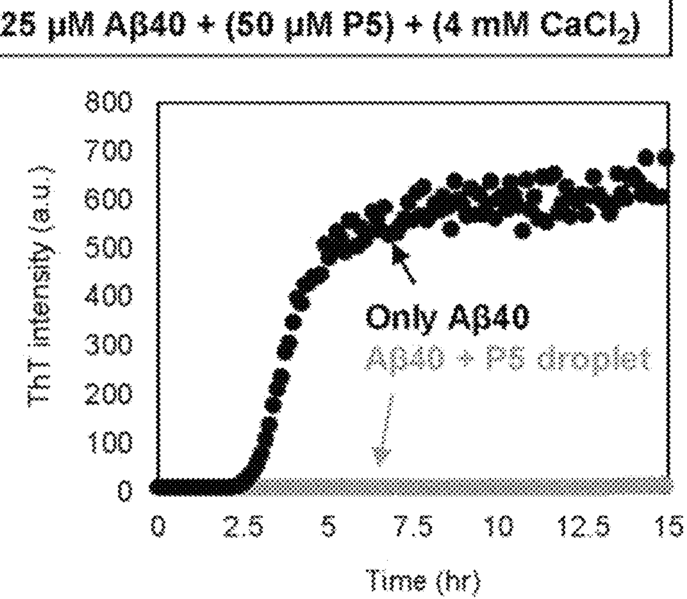

FIG. 21 shows that droplets suppress amyloid fibril formation. The vertical axis represents fluorescence intensity, the experiment uses thioflavin T for specifically detecting amyloid fibrils, and it is shown that the addition of droplets suppressed amyloid fibrils.

DESCRIPTION OF EMBODIMENTS

In the present invention, the term "protein" is used in a meaning including a polypeptide in which amino acids are polymerized via peptide bonds. In addition, herein, the term "protein" encompasses both of a protein modified with a glycan or the like and an unmodified protein, unless otherwise stated. The same applies to a protein that is not specified to be a protein.

Droplet

The present invention provides a droplet including an assembly of a protein, wherein the protein is a PDI family protein and/or an artificial protein, and contains a thioredoxin-like domain.

The "droplet" refers to an approximately spherical assembly in which a protein is liquid-liquid phase-separated, and in which the assembly of the protein has reversibility unlike an aggregation (aggregate) of an indefinite shape due to thermal denaturation or the like. When the protein assembles to form the droplet, the protein may optionally form the droplet in combination with a non-protein substance, such as a nucleic acid (e.g., DNA or RNA) or a crowder (e.g., ficol or glycerol). In addition, droplet formation also occurs through a temperature change or a pH change.

In the present invention, the "assembly" means that a protein accumulates. In a typical embodiment, the formation of the droplet occurs through: droplet formation through assembly of molecules at a molecular level; and droplet growth at a microscopically observable level through fusion of the droplets.

In addition, as described above, the assembly is an accumulation having reversibility of a protein unlike, for example, an aggregation of an indefinite shape of a protein due to thermal denaturation, chemical denaturation, or the like. Accordingly, the formation of the droplet through assembly of a protein and the breakdown of the droplet through dissociation of the protein for forming the droplet can be controlled by adjusting conditions in a surrounding environment (e.g., the concentration of a factor for promoting assembly, a temperature, a pH, and the excluded volume effect of a crowder).

In addition, typically, in a state of forming a droplet, proteins have fluidity unlike an aggregation, though interacting at such a distance as to be able to be brought into contact with each other. Accordingly, a dispersion, a droplet, and an aggregation of a protein are sometimes likened to three states of matter (gas, liquid, and solid). Specifically, a state in which a protein is dispersed in an aqueous solution is likened to a gas, a droplet, whose constituent components such as a protein have fluidity, is likened to a liquid, and an aggregation, which has no fluidity because of a strong interaction between constituent components, is likened to a solid. In addition, like water and oil undergo liquid-liquid phase separation (LLPS) instead of mixing with each other, biological phase separation refers to a situation in which droplet formation occurs via a protein. As described above, the "droplet", which is the subject matter of the present invention, is intended to be a mass formed by a protein that has reversibly assembled, not a particle of a liquid, such as water or an organic solvent, or a particle obtained by wrapping a liquid in a membrane such as a lipid bilayer. Accordingly, the droplet, which is a reversible assembly of a protein, is beginning to be reported as a multi-stage reaction field for an enzyme-substrate reaction or an efficient chemical reaction field, and finds use as a super-enhancer.

In the present invention, examples of the protein having a thioredoxin-like domain include a protein disulfide isomerase (PDI) family protein and an artificial protein. Those proteins may be used alone or in combination thereof. Examples of the PDI family protein include PDI, ERp46, ERp72, and P5. Of those, P5 or the like is preferred. Examples of the artificial protein include variants of the PDI family protein. The protein having a thioredoxin-like domain exists in all organisms, and examples thereof include those derived from: mammals, such as a human, a monkey, a mouse, a rat, a rabbit, a cat, a dog, a pig, a bovine, a horse, and a sheep; birds such as a chicken; and microorganisms such as yeast.

The protein having a thioredoxin-like domain preferably has a chaperone function. The "chaperone function" is a function of assisting appropriate folding of a protein, and the use of the protein having a chaperone function can be expected to suppress irreversible aggregation of the protein and to promote reversible assembly, and hence is preferred. In addition, hitherto, there has been no report that a droplet can be formed with a protein having both of enzyme activity and a chaperone function, and hence the present invention is also useful in such respect.

In a typical embodiment, the protein preferably has one or more thioredoxin-like domains. The lower limit of the number of thioredoxin-like domains per protein molecule is not limited, but is preferably 1 or more, more preferably 2 or more. The upper limit of the number of thioredoxin-like domains per protein molecule is also not limited, but is preferably 7 or less, more preferably 6 or less, still more preferably 5 or less, still more preferably 4 or less. The range of the number of thioredoxin-like domains per protein molecule is also not limited, but In the present invention, the "thioredoxin-like domain" plays an important role in various life reactions such as a redox reaction existing in all organisms. In the present invention, the molecular weight of the thioredoxin-like domain is, for example, from about 10 kDa to about 15 kDa, typically about 13 KDa. A thioredoxin-like domain having a redox-active CxxC motif can directly catalyze a redox reaction of a target molecule via the motif, and a thioredoxin-like domain having no redox-active CxxC motif is involved in substrate recognition or the like. Activity of reducing/cleaving a disulfide bond may be measured by, for example, a method described in Non-patent Literature 7.

Examples of the thioredoxin-like domain having activity of reducing/cleaving a disulfide bond include an a0 domain and an "a" domain in P5, which is a PDI family protein. In addition, the thioredoxin-like domain having activity of reducing/cleaving a disulfide bond preferably has the amino acid sequence of CGHC as shown in FIG. 20. Examples of the amino acid sequence of the a0 domain include: the amino acid sequence of the a0 domain of any one of various organisms shown in (the amino acid sequences of) FIG. 20; and an amino acid sequence having one or more (e.g., 1 to 5, 1 to 3, or 1 or 2) amino acids added, substituted, or deleted in the above-mentioned amino acid sequence. Examples of the amino acid sequence of the "a" domain include: the amino acid sequence of the "a" domain of any one of the various organisms shown in (the amino acid sequences of) FIG. 20; and an amino acid sequence having one or more (e.g., 1 to 5, 1 to 3, or 1 or 2) amino acids added, substituted, or deleted in the above-mentioned amino acid sequence. When the protein for forming the droplet has, as the thioredoxin-like domain, a domain formed of the above-mentioned amino acid sequence having one or more amino acids added, substituted, or deleted in the amino acid sequence of the a0 domain shown in FIG. 20, the position at which the amino acid is added, substituted, or deleted is preferably a position other than amino acids conserved in a plurality of biological species (e.g., other than amino acids conserved in 4 or more kinds, 5 or more kinds, 6 or more kinds, or all 7 kinds of the 7 kinds shown in FIG. 20)). When the protein for forming the droplet has, as the thioredoxin-like domain, a domain formed of the above-mentioned amino acid sequence having one or more amino acids added, substituted, or deleted in the amino acid sequence of the "a" domain shown in FIG. 20, the position at which the amino acid is added, substituted, or deleted is preferably a position other than amino acids conserved in a plurality of biological species (e.g., other than amino acids conserved in 4 or more kinds, 5 or more kinds, 6 or more kinds, or all 7 kinds of the 7 kinds shown in FIG. 20)).

An example of the thioredoxin-like domain having no activity of reducing/cleaving a disulfide bond is a "b" domain in P5. Examples of the amino acid sequence of the "b" domain include: the amino acid sequence of the "b" domain of any one of the various organisms shown in (the amino acid sequences of) FIG. 20; and an amino acid sequence having one or more (e.g., 1 to 5, 1 to 3, or 1 or 2)

amino acids added, substituted, or deleted in the above-mentioned amino acid sequence. When the protein for forming the droplet has, as the thioredoxin-like domain, a domain formed of the above-mentioned amino acid sequence having one or more amino acids added, substituted, or deleted in the amino acid sequence of the "b" domain shown in FIG. 20, the position at which the amino acid is added, substituted, or deleted is preferably a position other than amino acids conserved in a plurality of biological species (e.g., other than amino acids conserved in 4 or more kinds, 5 or more kinds, 6 or more kinds, or all 7 kinds of the 7 kinds shown in FIG. 20)).

In addition, in the present invention, the protein having a thioredoxin-like domain preferably has a region to which a factor for promoting assembly binds (assembly-promoting factor-binding region). Examples of the assembly-promoting factor include a calcium ion and other metal ions. Of those, a calcium ion or the like is preferred. Herein, the "assembly-promoting factor-binding region" means a region containing a sequence of E and D, and allowing the assembly-promoting factor to bind thereto. The assembly-promoting factor-binding region may be present in a region other than the thioredoxin-like domain or the like in the protein of the present invention, may be included in part of the thioredoxin-like domain or the like, or may satisfy both of the foregoing.

When the assembly-promoting factor is a calcium ion, the assembly-promoting factor-binding region is sometimes referred to as "calcium-binding region". The calcium-binding region may form a domain like an EF-hand domain. An example of the calcium-binding region is a calcium-binding region in P5. Examples of the amino acid sequence of the calcium-binding region in P5 include calcium-binding region portions in the amino acid sequences shown in FIG. 20, more specifically the amino acid sequences of PTIVEREPWDGRDGELPVEDDIDLSDVELDDLGKDEL (SEQ ID NO: 1), PTITPREPWDGKDGELPVEDDIDLSDVELDDLEKDEL (SEQ ID NO: 2), PKIHAVEPWDGKDGELPVEDDIDLSDVDLDDIWDKDEL (SEQ ID NO: 3), PTISTREPWDGKDGELPVEDDIDLSDVELDDLEKDEL (SEQ ID NO: 4), PAISVRDPWDGQDGVLPVEDDIDLSDVELDDLEKDEL (SEQ ID NO: 5), PKIHTVEAWDGKDGVLPVEDDIDLSDVDLDDLDKDEL (SEQ ID NO: 6), and PKINTVQAWDGKDGELPMEDDIDLSDVDLDDLEKDEL (SEQ ID NO: 7), and an amino acid sequence having one or more (e.g., 1 to 5, 1 to 3, or 1 or 2) amino acids added, substituted, or deleted in any one of the above-mentioned amino acid sequences. When the protein for forming the droplet has, as the calcium-binding region, a domain formed of the above-mentioned amino acid sequence having one or more amino acids added, substituted, or deleted in any one of the amino acid sequences of SEQ ID NOS: 1 to 7, the position at which the amino acid is added, substituted, or deleted is preferably a position other than amino acids conserved in a plurality of biological species (e.g., other than amino acids conserved in 4 or more kinds, 5 or more kinds, 6 or more kinds, or all 7 kinds of the 7 kinds shown in FIG. 20)).

In the present invention, the assembly-promoting factor-binding region (e.g., the calcium-binding region) may be included in part of any one of the thioredoxin-like domains, but the protein preferably has the assembly-promoting factor-binding region separate from the thioredoxin-like domains. In the present invention, the protein for forming the droplet preferably has: two thioredoxin-like domains each having activity of reducing/cleaving a disulfide bond; one thioredoxin-like domain having no activity of reducing/cleaving a disulfide bond; and one assembly-promoting factor-binding region.

In addition, in the present invention, the protein preferably has a linker sequence, for example, between a thioredoxin-like domain and another thioredoxin-like domain, between an assembly-promoting factor-binding region and another assembly-promoting factor-binding region, or between a thioredoxin-like domain and an assembly-promoting factor-binding region. In addition, the linker preferably contains at least one kind of amino acid residue selected from the group consisting of: serine; glycine; proline; glutamic acid; glutamine; aspartic acid; asparagine; arginine; lysine; and tyrosine. Any such amino acid residue is preferred because the amino acid residue hardly causes steric hindrance, and hence domains bound via the linker can each move flexibly to easily assume an arrangement appropriate for droplet formation. In addition, in the present invention, when the protein having a thioredoxin-like domain has a linker sequence, the linker sequence preferably has a certain length. By having a certain length, the linker sequence is predicted to lower the solubility of the thioredoxin-like domain to suitably contribute to droplet formation. Accordingly, when the protein having a thioredoxin-like domain has a linker sequence, at least one linker sequence (e.g., a linker sequence between the a0 domain and the "a" domain or a linker sequence between a "b" domain and the calcium-binding region to be described later) has preferably 5 or more amino acids, more preferably 25 or more amino acids. In addition, the upper limit of the length of each linker sequence is not particularly limited, but for example, is preferably 50 amino acids or less.

In addition, as the protein for forming the droplet, a signal sequence for endoplasmic reticulum localization may be fused to a protein having the above-mentioned domains. Examples of the signal sequence include amino acid sequences shown as signal sequences in FIG. 20 and an amino acid sequence having one or more (e.g., 1 to 5, 1 to 3, or 1 or 2) amino acids added, substituted, or deleted in any one of the above-mentioned amino acid sequences.

When P5 or a variant thereof is used as the protein for forming the droplet, the protein preferably contains all of the a0 domain, the "a" domain, and the "b" domain. In addition, examples of the amino acid sequence of such protein include: an amino acid sequence having the amino acid sequences of the a0 domain, "a" domain, "b" domain, and calcium-binding region of any one of the various organisms shown in FIG. 20 (preferred examples of such amino acid sequence also include: an amino acid sequence further having the linker sequence between the a0 domain and the "a" domain, the linker sequence between the "a" domain and the "b" domain, and the linker sequence between the "b" domain and the calcium-binding region; and an amino acid sequence also having the signal sequence in addition to the above-mentioned linker sequences); and an amino acid sequence having an amino acid sequence having one or more (e.g., 1 to 5, 1 to 3, or 1 or 2) amino acids added, substituted, or deleted in the above-mentioned amino acid sequence. When an amino acid is added, substituted, or deleted from the above-mentioned standard amino acids, an example of the position thereof is the above-mentioned position. In addition, examples of the protein for forming the droplet include: a protein having the amino acid sequence of P5 of any one of the various organisms shown in FIG. 20; and a protein having an amino acid sequence having one or more (e.g., 1 to 5, 1 to 3, or 1 or 2) amino acids added, substituted, or deleted in the above-mentioned amino acid sequence.

In addition, in the present invention, the protein having a thioredoxin-like domain may be a monomer, but preferably forms a dimer or a higher multimer (dimer, trimer, tetramer, or higher form). Herein, proteins forming a dimer or a higher multimer are sometimes collectively referred to as "multimers". In the present invention, the protein having a thioredoxin-like domain may be a mixture of two or more kinds selected from those monomers and multimers.

In addition, in the present invention, it is preferred that the protein for forming the droplet have an unstructured region, and have such a structure that at least one of the N- or C-terminus of the unstructured region is the thioredoxin-binding region. In addition, in the present invention, it is preferred that one calcium-binding site be present per monomer of the protein. It is particularly preferred that calcium bind to the unstructured region. The protein for forming the droplet of the present invention preferably has a structure having all of the above-mentioned three features.

In a typical embodiment of the present invention, the droplet has an approximately spherical form. In addition, in one embodiment of the present invention, the droplet preferably has an average particle diameter of 50 nm or more. In the present invention, partially because the droplets may be fused together, the upper limit of the average particle diameter of the droplets is not limited, but for example, is preferably 20 μm or less. In such embodiment, the average particle diameter may be measured using a dynamic light scattering apparatus, and more specifically, may be measured by a method described in Examples to be described later.

In the present invention, the droplet may be obtained in a state of being dispersed in an aqueous or organic liquid. Accordingly, the present invention also provides a dispersion liquid of a droplet. The dispersion liquid of a droplet of the present invention typically shows gel-like properties. The upper limit of the pH of the dispersion liquid of a droplet of the present invention is not particularly limited, but is preferably 10 or less, more preferably 9 or less, still more preferably 7.4 or less. In the dispersion liquid of the droplet of the present invention, the range of the pH is not particularly limited, but is, for example, preferably from 2 to 10, more preferably from 5 to 9, still more preferably from 6 to 7.4.

Method of Producing Droplet

The present invention provides a method of producing a droplet including a step of assembling a protein in the presence of an assembly-promoting factor, the protein being a PDI family protein and/or an artificial protein, and containing a thioredoxin-like domain. The assembly-promoting factor, the protein containing a thioredoxin-like domain, and the like are as described above.

The method of the present invention includes the step of assembling a protein in the presence of an assembly-promoting factor. In a typical embodiment, the step is performed by mixing the assembly-promoting factor and the protein. In addition, the step is generally performed in an aqueous or organic liquid, preferably an aqueous liquid. Examples of the aqueous liquid include water, ethanol, methanol, and trifluoroethanol. Examples of the organic liquid include formamide and ethylene glycol. Those liquids may be used alone or as a mixture thereof. For example, there may be used a mixture of water with at least one kind selected from the group consisting of: ethanol; methanol; and trifluoroethanol. In such embodiment, the blending ratio (v/v) of the at least one kind of hydrophilic liquid selected from the group consisting of: ethanol; methanol; and trifluoroethanol may be set to, for example, 15% or less, preferably 13% or less, more preferably 10% or less with respect to the volume of the mixed liquid of water and the hydrophilic liquid. In such embodiment, the blending ratio of the hydrophilic liquid may be set to, for example, 1% or more, preferably 3% or more, more preferably 5% or more with respect to the volume of the mixed liquid of water and the hydrophilic liquid. When the step is performed in a liquid, a component other than the protein having a thioredoxin-like domain and the assembly-promoting factor may be added to the liquid. Examples of the component other than the protein having a thioredoxin-like domain and the assembly-promoting factor include a pH adjusting agent, such as oxidized glutathione or reduced glutathione, and a buffering agent such as HEPES. Those components may be used alone or in combination thereof.

The usage amount of the protein having a thioredoxin-like domain is not particularly limited, but for example, when the step is performed in a liquid, is preferably 5 μM or more, more preferably 20 μM or more. The usage amount of the assembly-promoting factor is also not particularly limited, but when the step is performed in a liquid, is preferably 500 μM or more, more preferably 4 mM or more.

In the step, the upper limit of a pH is not particularly limited, but is preferably 10 or less, more preferably 9 or less, still more preferably 7.4 or less. In the step, the range of the pH is not particularly limited, but is, for example, preferably from 2 to 10, more preferably from 5 to 9, still more preferably from 6 to 7.4. A temperature when the step is performed is also not particularly limited, but is, for example, preferably from 0° C. to 70° C., more preferably from 0° C. to 20° C. A period of time for which the step is performed is also not particularly limited, but is, for example, preferably 1 minute or more, more preferably from 10 minutes to 60 minutes. When the step is performed, the protein having a thioredoxin-like domain assembles through the action of the assembly-promoting factor to form a droplet.

In the method of the present invention, a step of collecting the resultant droplet may be further performed. A method known per se (e.g., filtration, centrifugation, or chromatography) may be appropriately used.

EXAMPLES

Test Example 1

The base sequence of recombinant P5 having added thereto a His×6 tag was inserted between the restriction enzyme NdeI-BamHI sites of a pET15b vector for *Escherichia coli* expression (Novagen) to produce a plasmid. Competent cells BL21 (DE3) were transformed with the P5 plasmid, and then cultured in LA agar medium (LB agar medium+50 mg/L ampicillin) overnight at 37° C. A single colony was picked up from the agar medium and inoculated in 100 mL of LA medium (100 mL of LB medium+5 mg of ampicillin), and then subjected to shaking culture overnight at 37° C. 2 L of LB medium supplemented with 100 mg of ampicillin and 20 mL of the pre-culture broth was subjected to shaking culture for 4 hours at 37° C. After 4 hours (OD=about 0.5), isopropyl β-D-1-thiogalactopyranoside (IPTG) was added so as to achieve a final concentration of 0.5 mM, followed by further shaking culture for 4 hours at 37° C. After 4 hours, centrifugation was performed (5,000× g, 10 minutes, 4° C.) to collect the bacterial cells. The bacterial cells were lysed with a buffer (50 mM Tris/HCl, pH 8.1, 0.3 M NaCl, 1 mM phenylmethylsulfonyl fluoride), and then disrupted with a homogenizer. The disrupted solution was centrifuged (12,000×g, 20 min, 4° C.), the supernatant was further ultracentrifuged (38,000 rpm, 30 min, 4° C.), and the supernatant was collected. Ni-NTA Agarose (Qiagen) that had been equilibrated with a buffer (50 mM Tris/HCl, pH 8.1, 0.3 M NaCl) was added to the supernatant, and the mixture was stirred for 1 hour at 4° C. After 1 hour, the resultant was applied to an open column, washed twice with 40 mL of a buffer (50 mM Tris/HCl, pH 8.1, 0.3 M NaCl, 20 mM imidazole), and eluted 5 times with 10 mL of a buffer (50 mM Tris/HCl, pH 8.1, 0.3 M NaCl, 200 mM imidazole). The eluted sample was recognized by 10% SDS-PAGE, and then the eluted fraction of P5 was concentrated with Amicon Ultra (MWCO, 10,000: Millipore) to 500 μL. The concentrated sample was purified by being subjected to strong anion-exchange chromatography (MonoQ 10/100GL; GE Healthcare) utilizing an AKTA chromatography system (GE Helthcare). At that time, buffer A (50 mM Tris/HCl, pH 8.1, 1 mM EDTA) and buffer B (50 mM Tris/HCl, pH 8.1, 0.5 M NaCl, 1 mM EDTA) were used. The eluted sample was recognized by 10% SDS-PAGE, and then the eluted fraction of P5 was concentrated with Amicon Ultra (MWCO, 10,000: Millipore) to 250 μL. Further, the concentrate was purified by gel filtration chromatography (Superdex 200 10/300GL; GE Healthcare). At that time, a buffer (50 mM Tris/HCl, pH 8.1, 0.3 M NaCl, 1 mM EDTA) was used. The eluted sample was recognized by 10% SDS-PAGE, and then the eluted fraction of P5 was concentrated with Amicon Ultra (MWCO, 10,000: Millipore) to 500 μL, and the concentration was determined by a BCA method. Thus, a high-purity purified product was obtained (FIG. 1).

Figure 1:
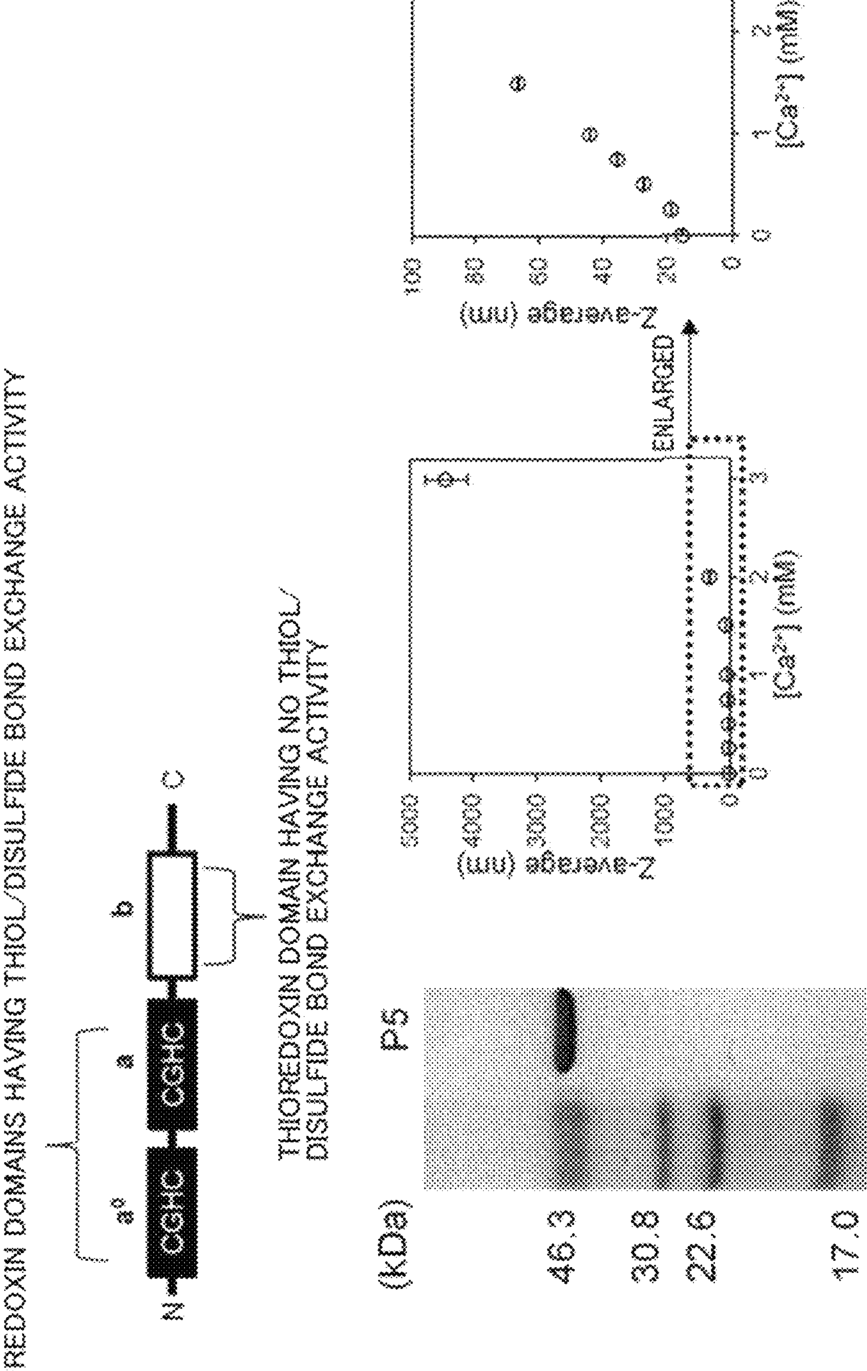

P5 as the high-purity purified product was titrated with calcium, and it was found with a dynamic light scattering (DLS) apparatus capable of evaluating a particle diameter that P5 associated in accordance with calcium titration (FIG. 1). A P5 protein solution was set to 50 mM HEPES at a pH of 7.2 and a protein concentration of 50 μM. Titration with EDTA serving as a chelating agent for calcium converts a calcium-dependent P5 associated state into P5 in a non-associated state (FIG. 2). According to the above-mentioned results, P5 can reversibly assemble in a calcium-dependent manner.

Test Example 2

The calcium-dependent associated bodies of P5 of Test Example 1 described above were subjected to phase-contrast observation with a confocal laser scanning biological microscope (FV1000, Olympus) fitted with an objective lens UCPLFLN 20×PH (NA0.7). The calcium-dependent P5 associated bodies were observed as nearly truly spherical particles. A situation in which the associated bodies fused together along with the passage of time was also observed, showing that the associated bodies grew (FIG. 3).

Test Example 3

Unlike an ordinary aggregation, a droplet has fluidity, and hence a substance moves in and out of the droplet. Fluorescence recovery after photobleaching (FRAP) is considered to be a general method for examining substance characteristics and associated molecular transport dynamics for droplet-like associated bodies (Bracha 2019 Nat Biotech). In view of this, in order to verify whether the calcium-dependent P5 associated bodies were droplets, a FRAP experiment was performed. At this time, in addition to the same composition as in Test Example 1 described above, a sample in which P5 having a fluorescent protein (mCherry) fused thereto (mCherry-P5) was allowed to coexist was prepared (50 mM HEPES, pH 7.5, 50 μM P5, 4 μM mCherry-P5), and observed in the same manner as in Test Example 2 (FIG. 4). mCherry-P5 was excited with a laser at 559 nm, and phase-contrast and fluorescence images were acquired. As shown in the upper part of FIG. 4, the fluorescence of mCherry-P5 was recognized in the P5 associated bodies observed in the phase-contrast images, showing that mCherry-P5 was incorporated into the P5 associated bodies. After that, the associated bodies were photobleached, and as a result, it was recognized that the fluorescence of the associated bodies was recovered along with a time change (lower part of FIG. 4. Measurement was performed 3 times, and a similar result was obtained every time. The lower left part of FIG. 4 shows a graph for one of those times. Statistical analysis results are shown in the lower right part of FIG. 4). The results show that mCherry-P5 bleached inside the associated bodies was discharged and intact mCherry-P5 newly flowed in from the outside, supporting that the calcium-dependent P5 associated bodies are droplets having fluidity.

Test Example 4

In order to verify optimal conditions for droplet formation, a search was made for the conditions of calcium and P5 concentrations. A solution of non-droplet P5 (5 μM to 100 μM P5) obtained by the method described in Test Example 1 and a calcium solution were mixed at various concentrations, and the mixture was left to stand still for 10 minutes. After that, the droplet was centrifuged at 15,000 g and 4° C. for 30 minutes to be fractionated into a precipitate, and the concentration of a supernatant fraction was calibrated. As a result, it was shown that, for P5 to form a droplet, a critical concentration was 20 μM, and calcium was appropriately 4 mM or more (FIG. 5).

Test Example 5

In order to identify a calcium-binding region, various mutants of P5 were produced and subjected to interaction analysis with an isothermal titration calorimeter ITC. In order to identify the calcium-binding site of P5, various mutants of P5 were produced as illustrated in FIG. 6, and an ITC experiment was performed under the conditions of 50 mM HEPES at a pH of 7.5. As a result, it was found that calcium bound to an unstructured region positioned at the C-terminus (FIG. 6).

Test Example 6

In order to perform real-time observation of droplet formation, a refractive index was measured using a tomocube (www.tomocube.com). Associated bodies of P5 were prepared in the same manner as in Test Example 1 except that 50 μM P5 and 4 mM $CaCl_2$) were added under the conditions of 50 mM HEPES at a pH of 7.2, and measurement was started within 10 minutes after the addition of $CaCl_2$). FIG. 7 shows images immediately after the start of the measurement (left part of FIG. 7), about 12 seconds after the start of the measurement (center of FIG. 7), and about 14 seconds thereafter (right part of FIG. 7). As a result, an image capturing the moment droplets are about to fuse together is shown at the center of FIG. 7. In addition, droplet surfaces are relatively rough, meaning high fluidity (FIG. 7).

Test Example 7

In order to verify whether various enzymes/chaperones and glutathione were able to be concentrated inside droplets, evaluation was performed through a refractive index with a tomocube and fluorescence observation. Associated bodies of P5 were prepared in the same manner as in Test Example 1 except for adding 50 μM P5 and 4 mM $CaCl_2$) under the conditions of 50 mM HEPES at a pH of 7.2, and measurement was performed within 10 minutes after the addition of $CaCl_2$). In addition, GFP-fused various enzymes/chaperones and fluorescently labeled glutathione were added at 5 μM. FIG. 8 supports the state of being droplets with a refractive index (RI), and indicates localization with various enzymes/chaperones and glutathione that are fluorescently labeled. It is shown that ERp46, ERp72, ERp57, and ERp44, which are enzymes/chaperones localized in the endoplasmic reticulum, are easily concentrated inside the droplets, but PDI hardly enters the inside of the droplets. In addition, it is shown that, through use of mCherry-ERp57 and GFP-ERp72, at least two kinds of enzymes/chaperones can be concentrated inside the droplets. In addition, glutathione labeled with ATTO 532 can also be concentrated inside the droplets (FIG. 8). As shown in FIG. 8, only PDI tends not to be incorporated into the inside of the droplets, but the other PDI family members can be concentrated. Accordingly, the droplets can concentrate other enzymes, and are expected to be applied to an industry involving using enzymes.

Test Example 8

P5 was titrated with calcium, and that P5 associated in accordance with calcium titration was evaluated in terms of the pH dependence of P5 droplet formation with a dynamic light scattering (DLS) apparatus capable of evaluating a particle diameter (FIG. 9). A P5 protein solution was set to 50 mM HEPES at a pH of 6.7, 7.0, 7.4, 7.6, 7.8, or 8.0, and a protein concentration of 50 μM. As shown in FIG. 9, a pH of 7.4 or less is preferred for droplet formation.

Test Example 9

P5 was titrated with calcium, and that P5 associated in accordance with calcium titration was evaluated in terms of the temperature dependence of P5 droplet formation with a dynamic light scattering (DLS) apparatus capable of evaluating a particle diameter (FIG. 10). A P5 protein solution was set to 50 mM HEPES at a pH of 7.5 and a protein concentration of 50 μM, and calcium titration was performed in the same manner as in Test Example 1 except for being performed at 10° C., 20° C., or 30° C. As shown in FIG. 10, a lower temperature is preferred for droplet formation.

Test Example 10

In order to identify an inner region of P5 required for titration formation, each mutant P5 illustrated in FIG. 11 was produced and evaluated for its functional site with a dynamic light scattering (DLS) apparatus capable of evaluating a particle diameter (FIG. 11). Calcium titration was performed in the same manner as in Test Example 1 except that P5 and mutant protein solutions were each used as 50 mM HEPES at a pH of 7.2 and a protein concentration of 50 μM. As shown in FIG. 11, full-length P5 is preferred for droplet formation.

Test Example 11

Amyloid fibril formation of 25 μM Aβ40 (amyloid beta 1-40, Peptide Institute, Inc.) was detected using a fluorescence plate reader having a stirring function (SH-9000Lab, Corona Electric). Specifically, Aβ40 was added at 25 μM to an aqueous solution (pH 7.2) containing 2.5 μM thioflavin T and 50 mM HEPES. Thioflavin T is a fluorescent molecule capable of detecting fibrils, and is capable of recognizing the progress of amyloid fibrils as shown in FIG. 21 ("only Aβ40" in FIG. 21). Meanwhile, when Aβ40 was added at 25 μM to an aqueous solution (pH 7.2) containing 2.5 μM thioflavin T and 50 mM HEPES and having P5 added thereto at 50 μM and Ca2+ added thereto at 4 mM, amyloid fibril formation was completely suppressed ("only Aβ40+P5 droplet" in FIG. 21). P5 forms a droplet under this condition, and hence it is found that the droplet functions as a chaperone that suppresses amyloid fibril formation.

Test Example 12. In order to extract structural information on P5 to which calcium did not bind, the full-length structure of P5 was determined by a small angle X-ray scattering method and X-ray crystallography (FIG. 12). The determination of the full-length structure of P5 was performed in accordance with a method described in Non-patent Literature 8. In order to prepare non-droplet P5, a solution of P5 obtained by the method described in Test Example 1 was subjected to gel filtration chromatography (Superdex 200 10/300GL; GE Healthcare) with a buffer (20 mM phosphate, pH 8.0, 150 mM NaCl, 5% glycerol) immediately before measurement. The eluted sample was concentrated to a concentration of 3 mg/mL using Amicon Ultra (MWCO, 10,000: Millipore). A small angle X-ray scattering (SAXS) experiment of non-droplet P5 was performed at SPring-8 BL45XU under the conditions of a detector PILATUS 3X 2M (DECTRIS), an X-ray wavelength of 1.0 Å, an X-ray exposure time of 1 second×20, a camera length of 2.0 m, and a temperature of 20.2° C., and each scattering pattern was obtained. A radius of gyration was calculated through the Guinier approximation of the scattering pattern, and a distance distribution function was obtained with GNOM software. On the basis of those data, the molecular structure of non-droplet P5 was constructed with GAJOE software. As a result, it was shown that flexibility was rich between thioredoxin-like domains, and that a dimer was formed. The dimer-formation region exhibits a leucine zipper motif according to the crystal structure, and the substitution of this site with alanine can produce a P5 mutant for forming a monomer (FIG. 13). The monomer P5 mutant also has an ability to form a droplet, though the ability to form a droplet is lower than that of the wild type (FIG. 14).

Test Example 13. In order to verify whether the P5 droplet was capable of concentrating low-molecular glutathione, a 500 μM solution of non-droplet P5 (final concentration: 50 μM P5) obtained by the method described in Test Example 1 was mixed with 50 mM HEPES at a pH of 7.5, 4 mM Ca, and [GSH]/[GSSG]=[1 mM]/[0.2 mM] at a ratio 1:9 (molar ratio) to achieve a final concentration of P5 of 50 μM, and the mixture was left to stand still for 30 minutes at 10° C. and centrifuged at 900 g for 15 minutes at 4° C., followed by the detection of the glutathione concentration of the supernatant. As a result, as compared to before the formation of droplets, nearly all glutathione disappeared and was incorporated into the droplets, indicating that glutathione was concentrated in P5 (FIG. 15).

Test Example 14. In order to verify folding catalysis in P5 droplets, Bovine Pancreatic Trypsin Inhibitor (BPTI) was adopted as a substrate. P5 not forming a droplet catalyzes the oxidative folding of BPTI (left part of FIG. 16). Meanwhile, under the condition that droplets were formed by mixing 500 μM non-droplet P5 with 50 mM HEPES at a pH of 7.5, 50 μM P5, 4 mM Ca, and [GSH]/[GSSG]=[1 mM]/[0.2 mM] at a ratio of 1:9 to achieve a final concentration of P5 of 50 μM, and leaving the mixture to stand still for 10 minutes at 37° C. to form droplets, followed by the addition of the substrate BPTI at 30 μM, it is found that the oxidative folding of BPTI did not progress in 1 minute, and BPTI was incorporated into the droplets (right part of FIG. 16). This means that the P5 droplets serve to concentrate and store a denatured substrate. In addition, 20 mM N-ethylmaleimide was added to the reaction liquid to stop the reaction, and detection was performed with a BPTI antibody. As a result, electrophoretic bands conceivably of a dimer and a trimer of BPTI were observed. Such reaction occurred conceivably due to the special situation in which glutathione was concentrated in the droplets of a protein having a thioredoxin-like domain.

Test Example 15. In order to examine the influences of organic solvents on P5 droplets, 5% v/v of methanol, ethanol, or trifluoroethanol was added to the P5 droplets obtained in Test Example 2, and the mixture was observed with a phase-contrast microscope. When an organic solvent is added at about 5% in v/v, the P5 droplets keep their shapes (FIG. 17). Although the droplets were produced using P5 in this Test Example, in view of the property by which a GFP-PDI family member added after the formation of the droplet P5 can be included thereinside, it is conceived that a PDI family protein and/or an artificial protein other than P5, the protein having a thioredoxin-like domain, can also produce a droplet.

Test Example 16. In order to examine the incorporation of a protein into P5 droplets, a mixed solution (molar ratio 1:5) of a PDI family protein having the fluorescent protein GFP fused thereto and P5, which was obtained in the same manner as in Test Example 1, was prepared and caused to form droplets by adding calcium, and then the resultant was centrifuged at 15,000×g for 15 minutes to be separated into a condensed layer (corresponding to the inside of the droplets) and a dilute layer (corresponding to the outside of the droplets). An absorbance at 488 nm before droplet formation, and the absorbance at 488 nm of the dilute layer after droplet formation/centrifugal separation were measured to calculate the ratio of the GFP-fused protein incorporated into the inside of the droplets. The results are shown in FIG. 18 and FIG. 19. The results of the test revealed that about 20% of the GFP-fused PDI family protein was incorporated into the P5 droplets.

INDUSTRIAL APPLICABILITY

Droplets such as an enzyme droplet (droplet formed by an enzymatic protein) can be expected to be applied in biopharmaceuticals, the beauty industry, industrial enzymes, and the food industry (e.g., the alcoholic beverage industry). More specifically, for example, droplet technologies can be expected to: be used in the quality control of a disulfide-containing protein preparation, such as insulin or an immunoglobulin, the restoration of a disulfide bond (e.g., hair repair), and the concentration and delivery of a redox molecule GSH; be used in the treatment of Parkinson's disease, diabetes, or the like; and be applied to a neurodegenerative disease through chaperone concentration. The novel droplet provided by the present invention can be applied in the above-mentioned fields, and hence is industrially extremely useful.

The invention claimed is:

1. A droplet comprising an assembly of a protein in the presence of a calcium ion, wherein the protein is a PDI family protein, and contains a thioredoxin-like domain, and wherein the protein has a calcium-binding region, wherein the protein is P5, wherein the droplet is only formed in vitro.

2. The droplet according to claim 1, wherein the protein has two or more thioredoxin-like domains, wherein at least two of the two or more thioredoxin-like domains are bound to each other via a linker, and wherein the linker contains at least one kind of amino acid residue selected from the group consisting of: serine; glycine; proline; glutamic acid; glutamine; aspartic acid; asparagine; arginine; lysine; and tyrosine.

3. The droplet according to claim 1, wherein the protein is a dimer or a higher multimer.

4. A method of producing a droplet comprising a step of assembling a protein in the presence of a calcium ion, the protein being a PDI family protein, and containing a thioredoxin-like domain, the protein further having a calcium-binding region, wherein the protein is P5.

5. The method according to claim 4, wherein at least two of the two or more thioredoxin-like domains are bound to each other via a linker, and wherein the linker contains at least one kind of amino acid residue selected from the group consisting of: serine; glycine; proline; glutamic acid; glutamine; aspartic acid; asparagine; arginine; lysine; and tyrosine.

6. The method according to claim 4, wherein the PDI family protein is a dimer or a higher multimer.

* * * * *

SEQUENCE LISTING

```
<160> NUMBER OF SEQ ID NOS: 21

<210> SEQ ID NO 1
<211> LENGTH: 37
<212> TYPE: PRT
<213> ORGANISM: Homo sapiens

<400> SEQUENCE: 1

Pro Thr Ile Val Glu Arg Glu Pro Trp Asp Gly Arg Asp Gly Glu Leu
1               5                   10                  15

Pro Val Glu Asp Asp Ile Asp Leu Ser Asp Val Glu Leu Asp Asp Leu
            20                  25                  30

Gly Lys Asp Glu Leu
        35


<210> SEQ ID NO 2
<211> LENGTH: 37
<212> TYPE: PRT
<213> ORGANISM: Mus musculus

<400> SEQUENCE: 2

Pro Thr Ile Thr Pro Arg Glu Pro Trp Asp Gly Lys Asp Gly Glu Leu
1               5                   10                  15

Pro Val Glu Asp Asp Ile Asp Leu Ser Asp Val Glu Leu Asp Asp Leu
            20                  25                  30

Glu Lys Asp Glu Leu
```

35

<210> SEQ ID NO 3
<211> LENGTH: 38
<212> TYPE: PRT
<213> ORGANISM: Gallus gallus

<400> SEQUENCE: 3

Pro Lys Ile His Ala Val Glu Pro Trp Asp Gly Lys Asp Gly Glu Leu
1               5                   10                  15

Pro Val Glu Asp Asp Ile Asp Leu Ser Asp Val Asp Leu Asp Asp Ile
            20                  25                  30

Trp Asp Lys Asp Glu Leu
        35

<210> SEQ ID NO 4
<211> LENGTH: 37
<212> TYPE: PRT
<213> ORGANISM: Bos taurus

<400> SEQUENCE: 4

Pro Thr Ile Ser Thr Arg Glu Pro Trp Asp Gly Lys Asp Gly Glu Leu
1               5                   10                  15

Pro Val Glu Asp Asp Ile Asp Leu Ser Asp Val Glu Leu Asp Asp Leu
            20                  25                  30

Glu Lys Asp Glu Leu
        35

<210> SEQ ID NO 5
<211> LENGTH: 37
<212> TYPE: PRT
<213> ORGANISM: Oryctolagus cuniculus

<400> SEQUENCE: 5

Pro Ala Ile Ser Val Arg Asp Pro Trp Asp Gly Gln Asp Gly Val Leu
1               5                   10                  15

Pro Val Glu Asp Asp Ile Asp Leu Ser Asp Val Glu Leu Asp Asp Leu
            20                  25                  30

Glu Lys Asp Glu Leu
        35

<210> SEQ ID NO 6
<211> LENGTH: 37
<212> TYPE: PRT
<213> ORGANISM: Ictalurus punctatus

<400> SEQUENCE: 6

Pro Lys Ile His Thr Val Glu Ala Trp Asp Gly Lys Asp Gly Val Leu
1               5                   10                  15

Pro Val Glu Asp Asp Ile Asp Leu Ser Asp Val Asp Leu Asp Asp Leu
            20                  25                  30

Asp Lys Asp Glu Leu
        35

<210> SEQ ID NO 7
<211> LENGTH: 37
<212> TYPE: PRT
<213> ORGANISM: Danio rerio

<400> SEQUENCE: 7

Pro Lys Ile Asn Thr Val Gln Ala Trp Asp Gly Lys Asp Gly Glu Leu

```
1               5                   10                  15

Pro Met Glu Asp Asp Ile Asp Leu Ser Asp Val Asp Leu Asp Asp Leu
            20                  25                  30

Glu Lys Asp Glu Leu
        35


<210> SEQ ID NO 8
<211> LENGTH: 440
<212> TYPE: PRT
<213> ORGANISM: Homo sapiens

<400> SEQUENCE: 8

Met Ala Leu Leu Val Leu Gly Leu Val Ser Cys Thr Phe Phe Leu Ala
1               5                   10                  15

Val Asn Gly Leu Tyr Ser Ser Ser Asp Asp Val Ile Glu Leu Thr Pro
            20                  25                  30

Ser Asn Phe Asn Arg Glu Val Ile Gln Ser Asp Ser Leu Trp Leu Val
        35                  40                  45

Glu Phe Tyr Ala Pro Trp Cys Gly His Cys Gln Arg Leu Thr Pro Glu
    50                  55                  60

Trp Lys Lys Ala Ala Thr Ala Leu Lys Asp Val Val Lys Val Gly Ala
65                  70                  75                  80

Val Asp Ala Asp Lys His His Ser Leu Gly Gly Gln Tyr Gly Val Gln
                85                  90                  95

Gly Phe Pro Thr Ile Lys Ile Phe Gly Ser Asn Lys Asn Arg Pro Glu
            100                 105                 110

Asp Tyr Gln Gly Gly Arg Thr Gly Glu Ala Ile Val Asp Ala Ala Leu
        115                 120                 125

Ser Ala Leu Arg Gln Leu Val Lys Asp Arg Leu Gly Gly Arg Ser Gly
    130                 135                 140

Gly Tyr Ser Ser Gly Lys Gln Gly Arg Ser Asp Ser Ser Ser Lys Lys
145                 150                 155                 160

Asp Val Ile Glu Leu Thr Asp Asp Ser Phe Asp Lys Asn Val Leu Asp
                165                 170                 175

Ser Glu Asp Val Trp Met Val Glu Phe Tyr Ala Pro Trp Cys Gly His
            180                 185                 190

Cys Lys Asn Leu Glu Pro Glu Trp Ala Ala Ala Ala Ser Glu Val Lys
        195                 200                 205

Glu Gln Thr Lys Gly Lys Val Lys Leu Ala Ala Val Asp Ala Thr Val
    210                 215                 220

Asn Gln Val Leu Ala Ser Arg Tyr Gly Ile Arg Gly Phe Pro Thr Ile
225                 230                 235                 240

Lys Ile Phe Gln Lys Gly Glu Ser Pro Val Asp Tyr Asp Gly Gly Arg
                245                 250                 255

Thr Arg Ser Asp Ile Val Ser Arg Ala Leu Asp Leu Phe Ser Asp Asn
            260                 265                 270

Ala Pro Pro Pro Glu Leu Leu Glu Ile Ile Asn Glu Asp Ile Ala Lys
        275                 280                 285

Arg Thr Cys Glu Glu His Gln Leu Cys Val Val Ala Val Leu Pro His
    290                 295                 300

Ile Leu Asp Thr Gly Ala Ala Gly Arg Asn Ser Tyr Leu Glu Val Leu
305                 310                 315                 320

Leu Lys Leu Ala Asp Lys Tyr Lys Lys Lys Met Trp Gly Trp Leu Trp
                325                 330                 335
```

```
Thr Glu Ala Gly Ala Gln Ser Glu Leu Glu Thr Ala Leu Gly Ile Gly
            340                 345                 350

Gly Phe Gly Tyr Pro Ala Met Ala Ala Ile Asn Ala Arg Lys Met Lys
        355                 360                 365

Phe Ala Leu Leu Lys Gly Ser Phe Ser Glu Gln Gly Ile Asn Glu Phe
    370                 375                 380

Leu Arg Glu Leu Ser Phe Gly Arg Gly Ser Thr Ala Pro Val Gly Gly
385                 390                 395                 400

Gly Ala Phe Pro Thr Ile Val Glu Arg Glu Pro Trp Asp Gly Arg Asp
                405                 410                 415

Gly Glu Leu Pro Val Glu Asp Asp Ile Asp Leu Ser Asp Val Glu Leu
            420                 425                 430

Asp Asp Leu Gly Lys Asp Glu Leu
        435                 440


<210> SEQ ID NO 9
<211> LENGTH: 440
<212> TYPE: PRT
<213> ORGANISM: Mus musculus

<400> SEQUENCE: 9

Met Ala Arg Leu Val Leu Gly Leu Val Ser Cys Thr Phe Phe Leu Ala
1               5                   10                  15

Val Ser Gly Leu Tyr Ser Ser Ser Asp Asp Val Ile Glu Leu Thr Pro
            20                  25                  30

Ser Asn Phe Asn Arg Glu Val Ile Gln Ser Asp Gly Leu Trp Leu Val
        35                  40                  45

Glu Phe Tyr Ala Pro Trp Cys Gly His Cys Gln Arg Leu Thr Pro Glu
    50                  55                  60

Trp Lys Lys Ala Ala Thr Ala Leu Lys Asp Val Val Lys Val Gly Ala
65                  70                  75                  80

Val Asn Ala Asp Lys His Gln Ser Leu Gly Gly Gln Tyr Gly Val Gln
                85                  90                  95

Gly Phe Pro Thr Ile Lys Ile Phe Gly Ala Asn Lys Asn Lys Pro Glu
            100                 105                 110

Asp Tyr Gln Gly Gly Arg Thr Gly Glu Ala Ile Val Asp Ala Ala Leu
        115                 120                 125

Ser Ala Leu Arg Gln Leu Val Lys Asp Arg Leu Gly Gly Arg Ser Gly
    130                 135                 140

Gly Tyr Ser Ser Gly Lys Gln Gly Arg Gly Asp Ser Ser Ser Lys Lys
145                 150                 155                 160

Asp Val Val Glu Leu Thr Asp Asp Thr Phe Asp Lys Asn Val Leu Asp
                165                 170                 175

Ser Glu Asp Val Trp Met Val Glu Phe Tyr Ala Pro Trp Cys Gly His
            180                 185                 190

Cys Lys Asn Leu Glu Pro Glu Trp Ala Ala Ala Ala Thr Glu Val Lys
        195                 200                 205

Glu Gln Thr Lys Gly Lys Val Lys Leu Ala Ala Val Asp Ala Thr Val
    210                 215                 220

Asn Gln Val Leu Ala Ser Arg Tyr Gly Ile Lys Gly Phe Pro Thr Ile
225                 230                 235                 240

Lys Ile Phe Gln Lys Gly Glu Ser Pro Val Asp Tyr Asp Gly Gly Arg
                245                 250                 255

Thr Arg Ser Asp Ile Val Ser Arg Ala Leu Asp Leu Phe Ser Asp Asn
            260                 265                 270
```

```
Ala Pro Pro Pro Glu Leu Leu Glu Ile Ile Asn Glu Asp Ile Ala Lys
        275                 280                 285

Lys Thr Cys Glu Glu His Gln Leu Cys Val Val Ala Val Leu Pro His
    290                 295                 300

Ile Leu Asp Thr Gly Ala Ala Gly Arg Asn Ser Tyr Leu Glu Val Leu
305                 310                 315                 320

Leu Lys Leu Ala Asp Lys Tyr Lys Lys Lys Met Trp Gly Trp Leu Trp
                325                 330                 335

Thr Glu Ala Gly Ala Gln Tyr Glu Leu Glu Asn Ala Leu Gly Ile Gly
            340                 345                 350

Gly Phe Gly Tyr Pro Ala Met Ala Ala Ile Asn Ala Arg Lys Met Lys
        355                 360                 365

Phe Ala Leu Leu Lys Gly Ser Phe Ser Glu Gln Gly Ile Asn Glu Phe
    370                 375                 380

Leu Arg Glu Leu Ser Phe Gly Arg Gly Ser Thr Ala Pro Val Gly Gly
385                 390                 395                 400

Gly Ser Phe Pro Thr Ile Thr Pro Arg Glu Pro Trp Asp Gly Lys Asp
                405                 410                 415

Gly Glu Leu Pro Val Glu Asp Asp Ile Asp Leu Ser Asp Val Glu Leu
            420                 425                 430

Asp Asp Leu Glu Lys Asp Glu Leu
        435                 440


<210> SEQ ID NO 10
<211> LENGTH: 447
<212> TYPE: PRT
<213> ORGANISM: Gallus gallus

<400> SEQUENCE: 10

Met Gly Val Arg Gly Thr Gly Gly Leu Trp Trp Gly Thr Val Ser Cys
1               5                   10                  15

Thr Leu Phe Leu Ala Val Asn Gly Leu Tyr Ser Ala Ser Asp Asp Val
            20                  25                  30

Ile Glu Leu Thr Pro Thr Asn Phe Asn Lys Glu Val Ile Gln Ser Glu
        35                  40                  45

Ser Leu Trp Leu Val Glu Phe Tyr Ala Pro Trp Cys Gly His Cys Gln
    50                  55                  60

Arg Leu Thr Pro Glu Trp Lys Lys Ala Ala Thr Ala Leu Lys Gly Val
65                  70                  75                  80

Val Lys Val Gly Ala Val Asp Ala Asp Lys His Gln Ser Leu Gly Gly
                85                  90                  95

Gln Tyr Gly Val Arg Gly Phe Pro Thr Ile Lys Ile Phe Gly Ala Asn
            100                 105                 110

Lys Asn Lys Ala Glu Asp Tyr Gln Gly Gly Arg Thr Ser Glu Ala Ile
        115                 120                 125

Val Asp Ala Ala Leu Ser Ala Leu Arg Ser Leu Val Lys Asp Arg Leu
    130                 135                 140

Ser Gly Arg Ser Gly Gly Tyr Ser Ser Gly Arg Gln Ser Arg Glu Ser
145                 150                 155                 160

Gly Gly Gly Asp Lys Lys Asp Val Ile Glu Leu Thr Asp Asp Ser Phe
                165                 170                 175

Asp Lys Asn Val Ile Asn Ser Asp Asp Val Trp Met Val Glu Phe Tyr
            180                 185                 190

Ala Pro Trp Cys Gly His Cys Lys Asn Leu Glu Pro Glu Trp Ala Ala
```

```
        195                 200                 205

Ala Ala Thr Glu Val Lys Glu Gln Thr Lys Gly Lys Val Lys Leu Ala
    210                 215                 220

Ala Val Asp Ala Thr Val Asn Gln Met Leu Ala Asn Arg Tyr Gly Ile
225                 230                 235                 240

Arg Gly Phe Pro Thr Ile Lys Ile Phe Gln Lys Gly Glu Asp Pro Val
                245                 250                 255

Asp Tyr Asp Gly Gly Arg Thr Arg Ser Asp Ile Thr Ala Arg Ala Leu
            260                 265                 270

Asp Leu Phe Ser Asp Asn Ala Pro Pro Pro Glu Leu Leu Glu Ile Ile
        275                 280                 285

Asn Glu Asp Val Leu Lys Thr Thr Cys Asp Ala His Gln Leu Cys Ile
    290                 295                 300

Ile Ser Val Leu Pro His Ile Leu Asp Thr Gly Ala Ser Gly Arg Asn
305                 310                 315                 320

Ser Tyr Leu Asp Val Met Leu Lys Met Ala Glu Lys Tyr Lys Lys Lys
                325                 330                 335

Met Trp Gly Trp Leu Trp Thr Glu Ala Gly Ala Gln Ser Asp Leu Glu
            340                 345                 350

Ser Ser Leu Gly Ile Gly Gly Phe Gly Tyr Pro Ala Met Ala Ala Ile
        355                 360                 365

Asn Ala Arg Lys Met Lys Phe Ala Leu Leu Lys Gly Ser Phe Ser Glu
    370                 375                 380

Gln Gly Ile Asn Glu Phe Leu Arg Glu Leu Ser Val Gly Arg Gly Ser
385                 390                 395                 400

Thr Ala Pro Val Gly Gly Gly Ala Phe Pro Lys Ile His Ala Val Glu
                405                 410                 415

Pro Trp Asp Gly Lys Asp Gly Glu Leu Pro Val Glu Asp Asp Ile Asp
            420                 425                 430

Leu Ser Asp Val Asp Leu Asp Asp Ile Trp Asp Lys Asp Glu Leu
        435                 440                 445


<210> SEQ ID NO 11
<211> LENGTH: 453
<212> TYPE: PRT
<213> ORGANISM: Bos taurus

<400> SEQUENCE: 11

Arg Arg Arg Leu Glu Cys Val Ala Ala Arg Ala Leu Ser Met Ala Arg
1               5                   10                  15

Leu Val Leu Gly Leu Met Ser Cys Thr Leu Phe Ile Thr Val Asn Gly
            20                  25                  30

Leu Tyr Ser Ser Ser Asp Asp Val Ile Glu Leu Thr Pro Ser Asn Phe
        35                  40                  45

Asn Arg Glu Val Ile Gln Ser Asp Ser Leu Trp Leu Val Glu Phe Tyr
    50                  55                  60

Ala Pro Trp Cys Gly His Cys Gln Arg Leu Thr Pro Glu Trp Lys Lys
65                  70                  75                  80

Ala Ala Thr Ala Leu Lys Asp Val Val Lys Val Gly Ala Val Asp Ala
                85                  90                  95

Asp Lys His Gln Ser Leu Gly Gly Gln Tyr Gly Val Gln Gly Phe Pro
            100                 105                 110

Thr Ile Lys Ile Phe Gly Ser Asn Lys Asn Lys Pro Glu Asp Tyr Gln
        115                 120                 125
```

```
Gly Gly Arg Thr Gly Glu Ala Ile Val Asp Ala Ala Leu Ser Ala Leu
    130                 135                 140

Arg Gln Leu Val Lys Asp Arg Leu Gly Gly Arg Gly Ser Gly Tyr Ser
145                 150                 155                 160

Ser Gly Lys Gln Gly Arg Gly Asp Ser Ser Ser Lys Lys Asp Val Ile
                165                 170                 175

Glu Leu Thr Asp Asp Asn Phe Asp Lys Asn Val Leu Asp Ser Glu Asp
            180                 185                 190

Val Trp Met Val Glu Phe Tyr Ala Pro Trp Cys Gly His Cys Lys Asn
        195                 200                 205

Leu Glu Pro Glu Trp Ala Ala Ala Ala Thr Glu Val Lys Glu Gln Thr
    210                 215                 220

Lys Gly Lys Val Lys Leu Ala Ala Val Asp Ala Thr Val Asn Gln Val
225                 230                 235                 240

Leu Ala Ser Arg Tyr Gly Ile Arg Gly Phe Pro Thr Ile Lys Ile Phe
                245                 250                 255

Gln Lys Gly Glu Ser Pro Val Asp Tyr Asp Gly Gly Arg Thr Arg Ser
            260                 265                 270

Asp Ile Val Ser Arg Ala Leu Asp Leu Phe Ser Asp Asn Ala Pro Pro
        275                 280                 285

Pro Glu Leu Leu Glu Ile Ile Asn Glu Asp Val Ala Lys Lys Thr Cys
    290                 295                 300

Glu Glu His Gln Leu Cys Val Val Ala Val Leu Pro His Ile Leu Asp
305                 310                 315                 320

Thr Gly Ala Ala Gly Arg Asn Ser Tyr Leu Glu Val Leu Leu Lys Leu
                325                 330                 335

Ala Asp Lys Tyr Lys Lys Lys Met Trp Gly Trp Leu Trp Thr Glu Ala
            340                 345                 350

Gly Ala Gln Ser Glu Leu Glu Asn Ala Leu Gly Ile Gly Gly Phe Gly
        355                 360                 365

Tyr Pro Ala Met Ala Ala Ile Asn Ala Arg Lys Met Lys Phe Ala Leu
    370                 375                 380

Leu Lys Gly Ser Phe Ser Glu Gln Gly Ile Asn Glu Phe Leu Arg Glu
385                 390                 395                 400

Leu Ser Phe Gly Arg Gly Ser Thr Ala Pro Val Gly Gly Gly Ala Phe
                405                 410                 415

Pro Thr Ile Ser Thr Arg Glu Pro Trp Asp Gly Lys Asp Gly Glu Leu
            420                 425                 430

Pro Val Glu Asp Asp Ile Asp Leu Ser Asp Val Glu Leu Asp Asp Leu
        435                 440                 445

Glu Lys Asp Glu Leu
    450


<210> SEQ ID NO 12
<211> LENGTH: 440
<212> TYPE: PRT
<213> ORGANISM: Oryctolagus cuniculus

<400> SEQUENCE: 12

Met Ala Arg Leu Gly Leu Gly Leu Val Ser Cys Thr Phe Phe Leu Ala
1               5                   10                  15

Val Asn Gly Leu Tyr Ser Ser Ser Asp Asp Val Ile Glu Leu Thr Pro
            20                  25                  30

Ser Asn Phe Asn Arg Glu Val Ile Gln Ser Asp Ser Leu Trp Leu Val
        35                  40                  45
```

```
Glu Phe Tyr Ala Pro Trp Cys Gly His Cys Gln Arg Leu Thr Pro Glu
    50                  55                  60

Trp Lys Lys Ala Ala Ser Ala Leu Lys Asp Val Val Lys Val Gly Ala
65                  70                  75                  80

Val Asp Ala Asp Lys His Gln Ala Leu Gly Gly Gln Tyr Gly Val Gln
                85                  90                  95

Gly Phe Pro Thr Ile Lys Ile Phe Gly Ala Asn Lys Asn Arg Pro Glu
            100                 105                 110

Asp Tyr Gln Gly Gly Arg Thr Gly Glu Ala Ile Val Asp Ala Ala Leu
        115                 120                 125

Ser Ala Leu Arg Gln Leu Val Lys Asp Arg Leu Gly Gly Arg Ser Gly
    130                 135                 140

Ser His Ser Ser Gly Arg Gln Gly Arg Gly Asp Ser Ala Ser Lys Lys
145                 150                 155                 160

Asp Val Ile Glu Leu Thr Asp Asp Ser Phe Asp Glu Asn Val Leu Glu
                165                 170                 175

Ser Asp Asp Ile Trp Met Val Glu Phe Tyr Ala Pro Trp Cys Gly His
            180                 185                 190

Cys Lys Asn Leu Glu Pro Glu Trp Ala Ala Ala Ala Thr Glu Val Lys
        195                 200                 205

Glu Gln Thr Lys Gly Lys Val Lys Leu Ala Ala Val Asp Ala Thr Val
    210                 215                 220

Asn Gln Met Leu Ser Ser Arg Tyr Gly Ile Arg Gly Phe Pro Thr Ile
225                 230                 235                 240

Lys Ile Phe Gln Lys Gly Glu Ser Pro Val Asp Tyr Asp Gly Gly Arg
                245                 250                 255

Thr Arg Ser Asp Ile Val Ser Arg Ala Leu Asp Leu Phe Ser Asp Asn
            260                 265                 270

Ala Pro Pro Pro Glu Leu Leu Glu Ile Val Asn Glu Asp Val Ala Lys
        275                 280                 285

Arg Ala Cys Glu Glu His Gln Leu Cys Ile Val Ala Val Leu Pro His
    290                 295                 300

Ile Leu Asp Thr Gly Ala Ala Gly Arg Asn Ser Tyr Leu Asp Val Leu
305                 310                 315                 320

Leu Lys Leu Ala Asp Lys Tyr Lys Lys Lys Met Trp Gly Trp Leu Trp
                325                 330                 335

Thr Glu Ala Gly Ala Gln Ala Glu Leu Glu Ser Ala Leu Gly Ile Gly
            340                 345                 350

Gly Phe Gly Tyr Pro Ala Met Ala Ala Ile Asn Ala Arg Lys Met Lys
        355                 360                 365

Phe Ala Leu Leu Lys Gly Ser Phe Ser Glu Gln Gly Ile Asn Glu Phe
    370                 375                 380

Leu Arg Glu Leu Ser Phe Gly Arg Gly Ser Thr Ala Pro Val Gly Gly
385                 390                 395                 400

Gly Val Phe Pro Ala Ile Ser Val Arg Asp Pro Trp Asp Gly Gln Asp
                405                 410                 415

Gly Val Leu Pro Val Glu Asp Asp Ile Asp Leu Ser Asp Val Glu Leu
            420                 425                 430

Asp Asp Leu Glu Lys Asp Glu Leu
        435                 440
```

<210> SEQ ID NO 13
<211> LENGTH: 439

```
<212> TYPE: PRT
<213> ORGANISM: Ictalurus punctatus

<400> SEQUENCE: 13

Met Arg Ala Phe Phe Gly Val Leu Ala Cys Ser Leu Thr Val Leu Ser
1               5                   10                  15

Val His Gly Leu Tyr Ser Ala Ser Asp Asp Val Ile Glu Leu Asn Pro
            20                  25                  30

Ser Asn Phe Asn Arg Glu Val Leu Gln Ser Asp Ser Leu Trp Leu Val
        35                  40                  45

Glu Phe Tyr Ala Pro Trp Cys Gly His Cys Gln Ser Leu Val Pro Glu
    50                  55                  60

Trp Lys Lys Ala Ala Thr Ala Leu Lys Gly Val Val Lys Val Gly Ala
65                  70                  75                  80

Val Asp Ala Asp Gln His Lys Ser Leu Gly Gly Gln Tyr Gly Val Arg
                85                  90                  95

Gly Phe Pro Thr Ile Lys Ile Phe Gly Ala Asn Lys His Lys Pro Glu
            100                 105                 110

Asp Tyr Gln Gly Gly Arg Ser Ser Gln Ala Ile Val Glu Ala Ala Leu
        115                 120                 125

Asn Ala Ala Arg Ser Leu Val Lys Asp Arg Leu Ser Gly Lys Ser Gly
    130                 135                 140

Gly Ser Asp Tyr Ser Arg Gln Ser Ser Gly Gly Gly Asn Lys Lys Asp
145                 150                 155                 160

Val Val Glu Leu Thr Asp Asp Asn Phe Asp Arg Met Val Leu Asp Gly
                165                 170                 175

Asp Ala Val Trp Met Val Glu Phe Phe Ala Pro Trp Cys Gly His Cys
            180                 185                 190

Lys Asn Leu Glu Pro Glu Trp Thr Ala Ala Ala Thr Gln Val Lys Glu
        195                 200                 205

Gln Thr Ser Gly Arg Val Lys Leu Gly Ala Val Asp Ala Thr Val His
    210                 215                 220

Gln Gly Leu Ala Ser Arg Tyr Gly Ile Lys Gly Phe Pro Thr Ile Lys
225                 230                 235                 240

Ile Phe Arg Lys Gly Glu Glu Pro Glu Asp Tyr Gln Gly Gly Arg Thr
                245                 250                 255

Arg Ser Asp Ile Ile Ala Arg Ala Ile Asp Leu Phe Ser Asp Asn Ala
            260                 265                 270

Pro Pro Pro Glu Leu Leu Glu Ile Leu Asn Glu Asp Ile Leu Lys Lys
        275                 280                 285

Thr Cys Glu Asp His Gln Leu Cys Ile Ile Ala Val Leu Pro His Ile
    290                 295                 300

Leu Asp Thr Gly Ala Ala Gly Arg Asn Ala Tyr Leu Glu Val Met Met
305                 310                 315                 320

Lys Met Ala Glu Lys Tyr Lys Lys Lys Met Trp Gly Trp Leu Trp Thr
                325                 330                 335

Glu Ser Gly Ala Gln Met Glu Leu Glu Ala Ser Leu Gly Ile Gly Gly
            340                 345                 350

Phe Gly Tyr Pro Ala Met Ala Ala Ile Asn Ala Arg Lys Met Lys Phe
        355                 360                 365

Ala Leu Leu Lys Gly Ser Phe Ser Glu Thr Gly Ile Tyr Glu Phe Leu
    370                 375                 380

Arg Asp Leu Ser Val Gly Arg Gly Ser Thr Ala Thr Ile Thr Gly Gly
385                 390                 395                 400
```

```
Ala Leu Pro Lys Ile His Thr Val Glu Ala Trp Asp Gly Lys Asp Gly
                405                 410                 415

Val Leu Pro Val Glu Asp Asp Ile Asp Leu Ser Asp Val Asp Leu Asp
            420                 425                 430

Asp Leu Asp Lys Asp Glu Leu
        435


<210> SEQ ID NO 14
<211> LENGTH: 440
<212> TYPE: PRT
<213> ORGANISM: Danio rerio

<400> SEQUENCE: 14

Met Arg Ala Leu Leu Gly Val Leu Ala Cys Ser Leu Thr Val Leu Ser
1               5                   10                  15

Ala Tyr Gly Leu Tyr Thr Ser Ser Asp Asp Val Val Glu Leu Asn Pro
            20                  25                  30

Ser Asn Phe Asn Arg Glu Val Ile Gln Ser Asp Ser Leu Trp Leu Val
        35                  40                  45

Glu Phe Tyr Ala Pro Trp Cys Gly His Cys Lys Ser Leu Ala Pro Glu
    50                  55                  60

Trp Lys Lys Ala Ala Thr Ala Leu Lys Gly Ile Val Lys Val Gly Ala
65                  70                  75                  80

Val Asp Ala Asp Gln His Asn Ser Leu Gly Gly Gln Tyr Gly Val Arg
                85                  90                  95

Gly Phe Pro Thr Ile Lys Ile Phe Gly Gly Asn Lys His Lys Pro Glu
            100                 105                 110

Asp Tyr Gln Gly Gly Arg Thr Asn Gln Ala Ile Val Asp Ala Ala Leu
        115                 120                 125

Asn Ala Leu Arg Ser Leu Val Lys Asp Arg Leu Gly Gly Lys Thr Gly
    130                 135                 140

Gly Ser Asp Tyr Ser Arg Gln Ser Gly Gly Gly Ala Gly Asn Lys Lys
145                 150                 155                 160

Asp Val Val Glu Leu Thr Asp Asp Asn Phe Asp Arg Thr Val Leu Glu
                165                 170                 175

Ser Asp Asp Val Trp Leu Val Glu Phe Phe Ala Pro Trp Cys Gly His
            180                 185                 190

Cys Lys Asn Leu Glu Pro Glu Trp Thr Ala Ala Ala Thr Glu Val Lys
        195                 200                 205

Glu Gln Thr Lys Gly Lys Val Lys Leu Ala Ala Val Asp Ala Thr Val
    210                 215                 220

His Gln Gly Leu Ala Ser Arg Phe Gly Ile Arg Gly Phe Pro Thr Ile
225                 230                 235                 240

Lys Val Phe Arg Lys Gly Glu Glu Pro Glu Asp Tyr Gln Gly Gly Arg
                245                 250                 255

Thr Arg Ser Asp Ile Val Ala Arg Ala Leu Glu Leu Tyr Ser Asp Asn
            260                 265                 270

Ile Pro Ala Pro Glu Leu Gln Glu Val Leu Asn Glu Gly Ile Leu Lys
        275                 280                 285

Lys Thr Cys Glu Asp Tyr Gln Leu Cys Ile Ile Ala Val Leu Pro His
    290                 295                 300

Ile Leu Asp Thr Gly Ala Ser Gly Arg Asn Ser Tyr Leu Glu Val Met
305                 310                 315                 320

Lys Thr Met Ala Glu Lys Tyr Lys Lys Lys Met Trp Gly Trp Leu Trp
```

```
                325                 330                 335

Thr Glu Ala Gly Ala Gln Met Glu Leu Glu Ala Ser Leu Gly Ile Gly
            340                 345                 350

Gly Phe Gly Tyr Pro Ala Met Ala Ala Ile Asn Ser Arg Lys Met Lys
        355                 360                 365

Phe Ala Leu Leu Lys Gly Ser Phe Ser Glu Thr Gly Ile His Glu Phe
    370                 375                 380

Leu Arg Glu Leu Ser Val Gly Arg Gly Ser Thr Ala Thr Val Gly Gly
385                 390                 395                 400

Gly Ala Leu Pro Lys Ile Asn Thr Val Gln Ala Trp Asp Gly Lys Asp
                405                 410                 415

Gly Glu Leu Pro Met Glu Asp Asp Ile Asp Leu Ser Asp Val Asp Leu
            420                 425                 430

Asp Asp Leu Glu Lys Asp Glu Leu
        435                 440


<210> SEQ ID NO 15
<211> LENGTH: 55
<212> TYPE: PRT
<213> ORGANISM: Homo sapiens

<400> SEQUENCE: 15

Pro Glu Asp Tyr Gln Gly Gly Arg Thr Gly Glu Ala Ile Val Asp Ala
1               5                   10                  15

Ala Leu Ser Ala Leu Arg Gln Leu Val Lys Asp Arg Leu Gly Gly Arg
            20                  25                  30

Ser Gly Gly Tyr Ser Ser Gly Lys Gln Gly Arg Ser Asp Ser Ser Ser
        35                  40                  45

Lys Lys Asp Val Ile Glu Leu
    50                  55


<210> SEQ ID NO 16
<211> LENGTH: 55
<212> TYPE: PRT
<213> ORGANISM: Mus musculus

<400> SEQUENCE: 16

Pro Glu Asp Tyr Gln Gly Gly Arg Thr Gly Glu Ala Ile Val Asp Ala
1               5                   10                  15

Ala Leu Ser Ala Leu Arg Gln Leu Val Lys Asp Arg Leu Gly Gly Arg
            20                  25                  30

Ser Gly Gly Tyr Ser Ser Gly Lys Gln Gly Arg Gly Asp Ser Ser Ser
        35                  40                  45

Lys Lys Asp Val Val Glu Leu
    50                  55


<210> SEQ ID NO 17
<211> LENGTH: 56
<212> TYPE: PRT
<213> ORGANISM: Gallus gallus

<400> SEQUENCE: 17

Ala Glu Asp Tyr Gln Gly Gly Arg Thr Ser Glu Ala Ile Val Asp Ala
1               5                   10                  15

Ala Leu Ser Ala Leu Arg Ser Leu Val Lys Asp Arg Leu Ser Gly Arg
            20                  25                  30

Ser Gly Gly Tyr Ser Ser Gly Arg Gln Ser Arg Glu Ser Gly Gly Gly
        35                  40                  45
```

```
Asp Lys Lys Asp Val Ile Glu Leu
    50                  55


<210> SEQ ID NO 18
<211> LENGTH: 55
<212> TYPE: PRT
<213> ORGANISM: Bos taurus

<400> SEQUENCE: 18

Pro Glu Asp Tyr Gln Gly Gly Arg Thr Gly Glu Ala Ile Val Asp Ala
1               5                   10                  15

Ala Leu Ser Ala Leu Arg Gln Leu Val Lys Asp Arg Leu Gly Gly Arg
            20                  25                  30

Gly Ser Gly Tyr Ser Ser Gly Lys Gln Gly Arg Gly Asp Ser Ser Ser
        35                  40                  45

Lys Lys Asp Val Ile Glu Leu
    50                  55


<210> SEQ ID NO 19
<211> LENGTH: 55
<212> TYPE: PRT
<213> ORGANISM: Oryctolagus cuniculus

<400> SEQUENCE: 19

Pro Glu Asp Tyr Gln Gly Gly Arg Thr Gly Glu Ala Ile Val Asp Ala
1               5                   10                  15

Ala Leu Ser Ala Leu Arg Gln Leu Val Lys Asp Arg Leu Gly Gly Arg
            20                  25                  30

Ser Gly Ser His Ser Ser Gly Arg Gln Gly Arg Gly Asp Ser Ala Ser
        35                  40                  45

Lys Lys Asp Val Ile Glu Leu
    50                  55


<210> SEQ ID NO 20
<211> LENGTH: 54
<212> TYPE: PRT
<213> ORGANISM: Ictalurus punctatus

<400> SEQUENCE: 20

Pro Glu Asp Tyr Gln Gly Gly Arg Ser Ser Gln Ala Ile Val Glu Ala
1               5                   10                  15

Ala Leu Asn Ala Ala Arg Ser Leu Val Lys Asp Arg Leu Ser Gly Lys
            20                  25                  30

Ser Gly Gly Ser Asp Tyr Ser Arg Gln Ser Ser Gly Gly Gly Asn Lys
        35                  40                  45

Lys Asp Val Val Glu Leu
    50


<210> SEQ ID NO 21
<211> LENGTH: 55
<212> TYPE: PRT
<213> ORGANISM: Danio rerio

<400> SEQUENCE: 21

Pro Glu Asp Tyr Gln Gly Gly Arg Thr Asn Gln Ala Ile Val Asp Ala
1               5                   10                  15

Ala Leu Asn Ala Leu Arg Ser Leu Val Lys Asp Arg Leu Gly Gly Lys
            20                  25                  30

Thr Gly Gly Ser Asp Tyr Ser Arg Gln Ser Gly Gly Gly Ala Gly Asn
```

-continued

```
        35                  40                  45

Lys Lys Asp Val Val Glu Leu
    50                  55
```